United States Patent
Horlick et al.

(10) Patent No.: US 9,328,166 B2
(45) Date of Patent: May 3, 2016

(54) ANTIBODIES DIRECTED AGAINST IL-17

(75) Inventors: Robert Horlick, San Diego, CA (US); David King, Encinitas, CA (US); Peter Bowers, San Diego, CA (US); Jennifer Dalton, Cardiff, CA (US); Betty Wu, San Diego, CA (US); Traci Roberts, San Diego, CA (US); Xue Zhang, San Diego, CA (US); Laurence Altobell, III, San Diego, CA (US)

(73) Assignee: AnaptysBio, Inc., San Diego, CA (US)

( * ) Notice: Subject to any disclaimer, the term of this patent is extended or adjusted under 35 U.S.C. 154(b) by 0 days.

(21) Appl. No.: 13/814,262

(22) PCT Filed: Aug. 2, 2011

(86) PCT No.: PCT/US2011/046201
§ 371 (c)(1),
(2), (4) Date: Feb. 19, 2013

(87) PCT Pub. No.: WO2012/018767
PCT Pub. Date: Feb. 9, 2012

(65) Prior Publication Data
US 2013/0202591 A1    Aug. 8, 2013

Related U.S. Application Data

(60) Provisional application No. 61/370,978, filed on Aug. 5, 2010.

(51) Int. Cl.
C07K 16/24 (2006.01)
A61K 39/00 (2006.01)

(52) U.S. Cl.
CPC ......... *C07K 16/244* (2013.01); *A61K 2039/505* (2013.01); *C07K 2317/21* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2008/0269467 A1 | 10/2008 | Allan et al. |
| 2009/0280131 A1 | 11/2009 | Di Padova et al. |
| 2010/0080812 A1 | 4/2010 | Auer et al. |

FOREIGN PATENT DOCUMENTS

| CN | 101001645 A | 7/2007 |
| JP | 2008-507988 A | 3/2008 |
| JP | 2009-519348 A | 5/2009 |
| WO | WO 2004050850 A2 * | 6/2004 |
| WO | WO 2006/013107 A1 | 2/2006 |
| WO | WO 2006013107 A1 * | 2/2006 |
| WO | WO 2007/117749 A2 | 10/2007 |
| WO | WO 2011/056864 A1 | 5/2011 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Betts et al (Bioinformatics for Geneticists, Eds MR Barnes and IC Gray. (Wiley, New York, 2003), pp. 289-316).*
Aggarwal et al., *J. Leukoc. Biol.*, 71 (1): 1-8 (2002).
Al et al., *BMC Biol.*, 6:13 (2008).
Antonysamy et al., *J. Immunol.*, 162: 577-584 (1999).
Chabaud et al., *Arthritis Rheum.*, 44: 1293-1303 (2001).
Fossiez, et al., *Int. Rev. Immunol.*, 16: 541 (1998).
Jovanovic et al., *J. Rheumatol.*, 28: 712-718 (2001).
Kolls et al., *Immunity*, 21: 467-476 (2004).
Kurasawa et al., *Arthritis Rheum.*, 43: 2455-2463 (2000).
Lubberts et al., *Arthritis & Rheumatism*, 50: 650-659 (2004).
Molet et al., *J. Allergy Clin. Immunol.*, 108: 430-438 (2001).
Moseley et al., *Cytokine Growth Factor Rev.*, 14(2): 155-74 (2003).
Rouvier et al., *J. Immunol.*, 150 (12): 5445-5456 (1993).
Starnes et al., *J. Immunol.*, 169 (2): 642-646 (2002).
Teunissen et al., *J. Invest. Dermatol.*, 111: 645-649 (1998).
Van Kooten et al., *J. Am. Soc. Nephrol.*, 9: 1526-1534 (1998).
Witowski et al., *Cell Mol. Life Sci.*, 61: 567-579 (2004).
Yao et al., *Immunity*, 3: 811 (1995).
People''s Republic of China, Office Action in Chinese Patent Application No. 201180048098.2 (May 6, 2014).
New Zealand Intellectual Property Office, Office Action in New Zealand Patent Application No. 607615 (Jul. 8, 2013).
New Zealand Intellectual Property Office, Office Action in New Zealand Patent Application No. 607615 (Oct. 23, 2014).
European Patent Office, Extended European Search Report in European Patent Application No. 11815158 (Jan. 30, 2014).
People's Republic of China, Office Action in Chinese Patent Application No. 201180048098.2 (Jan. 30, 2015).
New Zealand Intellectual Property Office, Office Action in New Zealand Patent Application No. 607615 (Jan. 26, 2015).
Kumagai et al., "Generation of Novel Functional Antibody Molecules by in vitro Selection System," *Protein, Nucleic Acid and Enzyme*, 43(2): 159-167 (Feb. 1, 1998).
Japanese Patent Office, Office Action in Japanese Patent Application No. 523260/2013 (Sep. 29, 2015).
Rudikoff et al., "Single amino acid substitution altering antigen-binding specificity," *Proc. Natl. Acad. Sci. USA*, 79: 1979-1983 (Mar. 1982).
Russian Federation Patent Office, Office Action in Russian Patent Application No. 2013109397 (Jul. 14, 2015).

* cited by examiner

*Primary Examiner* — Brian J Gangle
*Assistant Examiner* — Andrea McCollum
(74) *Attorney, Agent, or Firm* — Leydig, Voit & Mayer, Ltd.

(57) ABSTRACT

The invention relates to an isolated interleukin-17 (IL-17)-binding agent which comprises an immunoglobulin heavy chain polypeptide comprising SEQ ID NO: 1, SEQ ID NO: 32, SEQ ID NO: 33, SEQ ID NO: 78, or SEQ ID NO: 79, and an immunoglobulin light chain polypeptide comprising SEQ ID NO: 23, except that one or more specific of residues of SEQ ID NO: 1 and SEQ ID NO: 23 are replaced with a different residue. The invention also provides vectors, compositions, and methods of using the IL-17-binding agent to treat an IL-17-mediated disease.

23 Claims, 5 Drawing Sheets

SEQUENCE LISTING

```
<160> NUMBER OF SEQ ID NOS: 100

<210> SEQ ID NO 1
<211> LENGTH: 127
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 2
<211> LENGTH: 127
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
                20                  25                  30

Trp Met Ser Trp Val Arg Gln Ala Pro Gly Lys Gly Leu Glu Trp Val
            35                  40                  45

Ala Asn Ile Lys Glu Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 3
<211> LENGTH: 127
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
                20                  25                  30

Trp Met Thr Trp Val Arg Gln Ala Pro Gly Lys Gly Leu Glu Trp Val
            35                  40                  45

Ala Asn Ile Lys His Asp Gly Ser Glu Lys His Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
```

115 120 125

<210> SEQ ID NO 4
<211> LENGTH: 127
<212> TYPE: PRT
<213> ORGANISM: Artificial Sequence
<220> FEATURE:
<223> OTHER INFORMATION: Synthetic

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 5
<211> LENGTH: 127
<212> TYPE: PRT
<213> ORGANISM: Artificial Sequence
<220> FEATURE:
<223> OTHER INFORMATION: Synthetic

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Trp Met Thr Trp Val Arg Gln Ala Pro Gly Lys Gly Leu Glu Trp Val
        35                  40                  45

Ala Ala Ile Asn His Asp Gly Ser Glu Lys His Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 6
<211> LENGTH: 127
<212> TYPE: PRT
<213> ORGANISM: Artificial Sequence
<220> FEATURE:
<223> OTHER INFORMATION: Synthetic

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 7
<211> LENGTH: 127
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Val
        35                  40                  45

Ala Ser Ile Asn Glu Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 8
<211> LENGTH: 127
<212> TYPE: PRT
<213> ORGANISM: Artificial Sequence
<220> FEATURE:
<223> OTHER INFORMATION: Synthetic

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Trp Met Thr Trp Val Arg Gln Ala Pro Gly Lys Gly Leu Glu Trp Val
        35                  40                  45

Ala Ser Ile Asn His Asp Gly Ser Glu Lys His Tyr Val Gly Ser Val

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 9
<211> LENGTH: 127
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met Asn Trp Val Arg Gln Ala Pro Gly Lys Gly Leu Glu Trp Val
             35                  40                  45

Ala Ser Ile Asn Gln Asp Gly Ser Glu Lys Tyr Tyr Val Gly Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 10
<211> LENGTH: 127
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser His
                 20                  25                  30

Trp Met Ser Trp Val Arg Gln Ala Pro Gly Lys Gly Leu Glu Trp Val
             35                  40                  45

Ala Ser Ile Lys Glu Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110
```

```
Tyr Phe Asp Leu Trp Gly Arg Gly Thr Leu Val Thr Val Ser Ser
        115                 120                 125

<210> SEQ ID NO 11
<211> LENGTH: 127
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Thr Trp Val Arg Gln Ala Pro Gly Lys Gly Leu Glu Trp Val
        35                  40                  45

Ala Ser Ile Lys His Asp Gly Ser Glu Lys His Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 12
<211> LENGTH: 127
<212> TYPE: PRT
<213> ORGANISM: Artificial Sequence
<220> FEATURE:
<223> OTHER INFORMATION: Synthetic

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Ala Asn Ile Arg Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 13
<211> LENGTH: 127
<212> TYPE: PRT
<213> ORGANISM: Artificial Sequence
<220> FEATURE:
<223> OTHER INFORMATION: Synthetic
```

<400> SEQUENCE: 13

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Trp Met Asp Trp Val Arg Gln Ala Pro Gly Lys Gly Leu Glu Trp Val
        35                  40                  45
Ala Ser Ile Arg Glu Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Tyr Tyr Asp Ile Leu Thr Asp Tyr Tyr Ile His Tyr Trp
            100                 105                 110
Tyr Phe Asp Leu Trp Gly Arg Gly Thr Leu Val Thr Val Ser Ser
        115                 120                 125
```

<210> SEQ ID NO 14
<211> LENGTH: 127
<212> TYPE: PRT
<213> ORGANISM: Artificial Sequence
<220> FEATURE:
<223> OTHER INFORMATION: Synthetic

<400> SEQUENCE: 14

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Asp Trp Val Arg Gln Ala Pro Gly Lys Gly Leu Glu Trp Val
        35                  40                  45
Ala Asn Ile Arg Glu Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Tyr Tyr Asp Ile Leu Thr Asp Tyr Tyr Ile His Tyr Trp
            100                 105                 110
Tyr Phe Asp Leu Trp Gly Arg Gly Thr Leu Val Thr Val Ser Ser
        115                 120                 125
```

<210> SEQ ID NO 15
<211> LENGTH: 127
<212> TYPE: PRT
<213> ORGANISM: Artificial Sequence
<220> FEATURE:
<223> OTHER INFORMATION: Synthetic

<400> SEQUENCE: 15

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Asp Trp Val Arg Gln Ala Pro Gly Lys Gly Leu Glu Trp Val
        35                  40                  45
```

```
Ala Ser Ile Arg Glu Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
                115                 120                 125
```

<210> SEQ ID NO 16
<211> LENGTH: 127
<212> TYPE: PRT
<213> ORGANISM: Artificial Sequence
<220> FEATURE:
<223> OTHER INFORMATION: Synthetic

<400> SEQUENCE: 16

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Trp Met Asp Trp Val Arg Gln Ala Pro Gly Lys Gly Leu Glu Trp Val
                 35                  40                  45

Ala Ala Ile Arg Glu Asp Gly Ser Glu Lys Tyr Tyr Val Gly Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
                115                 120                 125
```

<210> SEQ ID NO 17
<211> LENGTH: 127
<212> TYPE: PRT
<213> ORGANISM: Artificial Sequence
<220> FEATURE:
<223> OTHER INFORMATION: Synthetic

<400> SEQUENCE: 17

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Trp Met Asp Trp Val Arg Gln Ala Pro Gly Lys Gly Leu Glu Trp Val
                 35                  40                  45

Ala Ser Ile Arg Glu Asp Gly Ser Glu Lys Tyr Tyr Val Gly Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Ile Leu Thr Asp Tyr Tyr Ile His Tyr Trp
                100                 105                 110
```

Tyr Phe Asp Leu Trp Gly Arg Gly Thr Leu Val Thr Val Ser Ser
         115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asp Trp Val Arg Gln Ala Pro Gly Lys Gly Leu Glu Trp Val
        35                  40                  45

Ala Ala Ile Arg Glu Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
         115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Synthetic

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asp Trp Val Arg Gln Ala Pro Gly Lys Gly Leu Glu Trp Val
        35                  40                  45

Ala Ser Ile Arg Glu Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
         115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Asp Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 21
<211> LENGTH: 127
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Glu Ile Val Thr Asp Tyr His Val His Tyr Trp
            100                 105                 110

Tyr Phe Asn Leu Trp Gly Arg Gly Thr Leu Val Thr Val Ser Ser
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

```
Ala Asn Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr His Asp Ile Val Thr Asp Ser Tyr Val His Ser Trp
            100                 105                 110

Tyr Phe Glu Leu Trp Gly Arg Gly Thr Leu Val Thr Val Ser Ser
            115                 120                 125
```

<210> SEQ ID NO 23
<211> LENGTH: 25
<212> TYPE: PRT
<213> ORGANISM: Homo sapiens

<400> SEQUENCE: 23

```
Ala Val Tyr Tyr Cys Gln Gln Tyr Gly Ser Ser Pro Cys Thr Phe Gly
 1               5                  10                  15

Gln Gly Thr Arg Leu Glu Ile Lys Arg
            20                  25
```

<210> SEQ ID NO 24
<211> LENGTH: 109
<212> TYPE: PRT
<213> ORGANISM: Artificial Sequence
<220> FEATURE:
<223> OTHER INFORMATION: Synthetic

<400> SEQUENCE: 24

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys Arg
            100                 105
```

<210> SEQ ID NO 25
<211> LENGTH: 109
<212> TYPE: PRT
<213> ORGANISM: Artificial Sequence
<220> FEATURE:
<223> OTHER INFORMATION: Synthetic

<400> SEQUENCE: 25

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
         35                  40                  45
```

```
Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Ser Thr Pro
                85                  90                  95

Leu Thr Phe Gly Gly Gly Thr Lys Val Glu Ile Lys Arg
                100                 105
```

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg
                100                 105
```

<210> SEQ ID NO 27
<211> LENGTH: 114
<212> TYPE: PRT
<213> ORGANISM: Artificial Sequence
<220> FEATURE:
<223> OTHER INFORMATION: Synthetic

<400> SEQUENCE: 27

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Gly Ser Ser Pro Leu Thr Phe Gly Gly Gly Thr Lys Val Glu Ile
                100                 105                 110

Lys Arg
```

<210> SEQ ID NO 28

<211> LENGTH: 109
<212> TYPE: PRT
<213> ORGANISM: Artificial Sequence
<220> FEATURE:
<223> OTHER INFORMATION: Synthetic

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys Arg
            100                 105

<210> SEQ ID NO 29
<211> LENGTH: 109
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105

<210> SEQ ID NO 30
<211> LENGTH: 127
<212> TYPE: PRT
<213> ORGANISM: Artificial Sequence
<220> FEATURE:
<223> OTHER INFORMATION: Synthetic

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 31
<211> LENGTH: 127
<212> TYPE: PRT
<213> ORGANISM: Artificial Sequence
<220> FEATURE:
<223> OTHER INFORMATION: Synthetic

<400> SEQUENCE: 31

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Trp Met Asn Trp Val Arg Gln Ala Pro Gly Lys Gly Leu Glu Trp Val
         35                  40                  45

Ala Ala Ile Asn Gln Asp Gly Ser Glu Lys Tyr Tyr Val Gly Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 32
<211> LENGTH: 127
<212> TYPE: PRT
<213> ORGANISM: Artificial Sequence
<220> FEATURE:
<223> OTHER INFORMATION: Synthetic

<400> SEQUENCE: 32

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Thr Pro Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
```

<210> SEQ ID NO 33
<211> LENGTH: 127
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 34
<211> LENGTH: 127
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Thr Pro Gly Lys Gly Leu Glu Trp Val
        35                  40                  45

Ala Ser Ile Lys Gln Asp Gly Ser Glu Lys Tyr Tyr Val Asp Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 35
<211> LENGTH: 127
<212> TYPE: PRT
<213> ORGANISM: Artificial Sequence
<220> FEATURE:
<223> OTHER INFORMATION: Synthetic

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Thr Pro Gly Lys Gly Leu Glu Trp Val
        35                  40                  45

Ala Ser Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 36
<211> LENGTH: 127
<212> TYPE: PRT
<213> ORGANISM: Artificial Sequence
<220> FEATURE:
<223> OTHER INFORMATION: Synthetic

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ala Ser Ile Lys Glu Asp Gly Ser Glu Lys Tyr Tyr Val Asp Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 37
<211> LENGTH: 127
<212> TYPE: PRT
<213> ORGANISM: Artificial Sequence
<220> FEATURE:
<223> OTHER INFORMATION: Synthetic

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Thr Pro Gly Lys Gly Leu Glu Trp Val
        35                  40                  45

Ala Ser Ile Lys Glu Asp Gly Ser Glu Lys Tyr Tyr Val Asp Ser Val

```
                    50                  55                  60
Lys Val Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 38
<211> LENGTH: 127
<212> TYPE: PRT
<213> ORGANISM: Artificial Sequence
<220> FEATURE:
<223> OTHER INFORMATION: Synthetic

<400> SEQUENCE: 38

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
                20                  25                  30

Trp Met Ser Trp Val Arg Gln Thr Pro Gly Lys Gly Leu Glu Trp Val
            35                  40                  45

Ala Ser Ile Lys Glu Asp Gly Ser Glu Lys Tyr Tyr Val Asp Ser Val
        50                  55                  60

Lys Val Arg Phe Ile Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 39
<211> LENGTH: 127
<212> TYPE: PRT
<213> ORGANISM: Artificial Sequence
<220> FEATURE:
<223> OTHER INFORMATION: Synthetic

<400> SEQUENCE: 39

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
                20                  25                  30

Trp Met Ser Trp Val Arg Gln Thr Pro Gly Lys Gly Leu Glu Trp Val
            35                  40                  45

Ala Ser Ile Lys Glu Asp Gly Ser Glu Lys Tyr Tyr Val Asp Ser Val
        50                  55                  60

Lys Val Arg Phe Thr Ile Ser Arg Asp Asn Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110
```

```
Tyr Phe Asp Leu Trp Gly Arg Gly Thr Leu Val Thr Val Ser Ser
            115                 120                 125

<210> SEQ ID NO 40
<211> LENGTH: 127
<212> TYPE: PRT
<213> ORGANISM: Artificial Sequence
<220> FEATURE:
<223> OTHER INFORMATION: Synthetic

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Thr Pro Gly Lys Gly Leu Glu Trp Val
        35                  40                  45

Ala Ser Ile Lys Glu Asp Gly Ser Glu Lys Tyr Tyr Val Asp Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 41
<211> LENGTH: 127
<212> TYPE: PRT
<213> ORGANISM: Artificial Sequence
<220> FEATURE:
<223> OTHER INFORMATION: Synthetic

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Thr Pro Gly Lys Gly Leu Glu Trp Val
        35                  40                  45

Ala Ser Ile Lys Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 42
<211> LENGTH: 127
<212> TYPE: PRT
<213> ORGANISM: Artificial Sequence
<220> FEATURE:
<223> OTHER INFORMATION: Synthetic
```

```
<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Thr Pro Gly Lys Gly Leu Glu Trp Val
        35                  40                  45

Ala Ser Ile Lys Glu Asp Gly Ser Glu Lys Tyr Tyr Val Gly Ser Val
    50                  55                  60

Lys Val Arg Phe Ile Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 43
<211> LENGTH: 127
<212> TYPE: PRT
<213> ORGANISM: Artificial Sequence
<220> FEATURE:
<223> OTHER INFORMATION: Synthetic

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Thr Pro Gly Lys Gly Leu Glu Trp Val
        35                  40                  45

Ala Ser Ile Lys Glu Asp Gly Ser Glu Lys Tyr Tyr Val Asp Ser Val
    50                  55                  60

Lys Val Arg Phe Ile Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 44
<211> LENGTH: 127
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser His
            20                  25                  30

Trp Met Ser Trp Val Arg Gln Ala Pro Gly Lys Gly Leu Glu Trp Val
        35                  40                  45
```

```
Ala Ser Ile Lys Glu Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
                115                 120                 125

<210> SEQ ID NO 45
<211> LENGTH: 127
<212> TYPE: PRT
<213> ORGANISM: Artificial Sequence
<220> FEATURE:
<223> OTHER INFORMATION: Synthetic

<400> SEQUENCE: 45

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser His
                 20                  25                  30

Trp Met Ser Trp Val Arg Gln Ala Pro Gly Lys Gly Leu Glu Trp Val
             35                  40                  45

Ala Ser Ile Lys Glu Asp Gly Ser Glu Lys Tyr Tyr Val Asp Ser Val
         50                  55                  60

Lys Gly Arg Phe Thr Ile Ser Arg Asp Asn Asp Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
                115                 120                 125

<210> SEQ ID NO 46
<211> LENGTH: 127
<212> TYPE: PRT
<213> ORGANISM: Artificial Sequence
<220> FEATURE:
<223> OTHER INFORMATION: Synthetic

<400> SEQUENCE: 46

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn His
                 20                  25                  30

Trp Met Asn Trp Val Arg Gln Thr Pro Gly Lys Gly Leu Glu Trp Val
             35                  40                  45

Ala Ala Ile Asn Glu Asp Gly Ser Glu Lys Tyr Tyr Val Gly Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Asp Tyr Tyr Asp Ile Leu Thr Asp Tyr Tyr Ile His Tyr Trp
                100                 105                 110
```

Tyr Phe Asp Leu Trp Gly Arg Gly Thr Leu Val Thr Val Ser Ser
            115                 120                 125

<210> SEQ ID NO 47
<211> LENGTH: 127
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 48
<211> LENGTH: 127
<212> TYPE: PRT
<213> ORGANISM: Artificial Sequence
<220> FEATURE:
<223> OTHER INFORMATION: Synthetic

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 49
<211> LENGTH: 127
<212> TYPE: PRT
<213> ORGANISM: Artificial Sequence
<220> FEATURE:
<223> OTHER INFORMATION: Synthetic

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Gly Arg Phe Ile Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

<210> SEQ ID NO 50
<211> LENGTH: 127
<212> TYPE: PRT
<213> ORGANISM: Artificial Sequence
<220> FEATURE:
<223> OTHER INFORMATION: Synthetic

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ser Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Leu Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

<210> SEQ ID NO 51
<211> LENGTH: 127
<212> TYPE: PRT
<213> ORGANISM: Artificial Sequence
<220> FEATURE:
<223> OTHER INFORMATION: Synthetic

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45
```

```
Ala Ser Ile Asn Glu Asp Gly Ser Glu Lys Tyr Tyr Val Gly Ser Val
        50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 52
<211> LENGTH: 127
<212> TYPE: PRT
<213> ORGANISM: Artificial Sequence
<220> FEATURE:
<223> OTHER INFORMATION: Synthetic

<400> SEQUENCE: 52

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
                 20                  25                  30

Trp Met Asn Trp Val Arg Gln Thr Pro Gly Lys Gly Leu Glu Trp Val
             35                  40                  45

Ala Ala Ile Asn Glu Asp Gly Ser Glu Lys Tyr Tyr Val Gly Ser Val
        50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Leu Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 53
<211> LENGTH: 127
<212> TYPE: PRT
<213> ORGANISM: Artificial Sequence
<220> FEATURE:
<223> OTHER INFORMATION: Synthetic

<400> SEQUENCE: 53

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
                 20                  25                  30

Trp Met Asn Trp Val Arg Gln Thr Pro Gly Lys Gly Leu Glu Trp Val
             35                  40                  45

Ala Ala Ile Asn Glu Asp Gly Ser Glu Lys Tyr Tyr Val Gly Ser Val
        50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Thr Arg Asp Tyr Tyr Asp Ile Leu Thr Asp Tyr Tyr Ile His Tyr Trp
```

Tyr Phe Asp Leu Trp Gly Arg Gly Thr Leu Val Thr Val Ser Ser
            115                 120                 125

<210> SEQ ID NO 54
<211> LENGTH: 127
<212> TYPE: PRT
<213> ORGANISM: Artificial Sequence
<220> FEATURE:
<223> OTHER INFORMATION: Synthetic

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Phe Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 55
<211> LENGTH: 127
<212> TYPE: PRT
<213> ORGANISM: Artificial Sequence
<220> FEATURE:
<223> OTHER INFORMATION: Synthetic

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 56
<211> LENGTH: 127
<212> TYPE: PRT
<213> ORGANISM: Artificial Sequence
<220> FEATURE:

<400> SEQUENCE: 56

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn His
            20                  25                  30
Trp Met Asn Trp Val Arg Gln Thr Pro Gly Lys Gly Leu Glu Trp Val
        35                  40                  45
Ala Ala Ile Asn Glu Asp Gly Ser Glu Lys Tyr Tyr Val Gly Ser Val
    50                  55                  60
Lys Val Arg Phe Ile Ile Ser Arg Asp Asn Ala Lys Asn Ser Leu Tyr
65                  70                  75                  80
Leu Gln Met Asn Ser Leu Arg Val Glu Asp Thr Ala Val Tyr Tyr Cys
                85                  90                  95
Ala Arg Asp Tyr Tyr Asp Ile Leu Thr Asp Tyr Tyr Ile His Tyr Trp
            100                 105                 110
Tyr Phe Asp Leu Trp Gly Arg Gly Thr Leu Val Thr Val Ser Ser
        115                 120                 125
```

<210> SEQ ID NO 57
<211> LENGTH: 127
<212> TYPE: PRT
<213> ORGANISM: Artificial Sequence
<220> FEATURE:
<223> OTHER INFORMATION: Synthetic

<400> SEQUENCE: 57

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn His
            20                  25                  30
Trp Met Asn Trp Val Arg Gln Thr Pro Gly Lys Gly Leu Glu Trp Val
        35                  40                  45
Ala Ala Ile Asn Glu Asp Gly Ser Glu Lys Tyr Tyr Val Gly Ser Val
    50                  55                  60
Lys Val Arg Phe Thr Ile Ser Arg Asp Asn Ala Lys Asn Ser Val Tyr
65                  70                  75                  80
Leu Gln Met Asn Ser Leu Arg Val Glu Asp Thr Ala Val Tyr Tyr Cys
                85                  90                  95
Ala Arg Asp Tyr Tyr Asp Ile Leu Thr Asp Tyr Tyr Ile His Tyr Trp
            100                 105                 110
Tyr Phe Asp Leu Trp Gly Arg Gly Thr Leu Val Thr Val Ser Ser
        115                 120                 125
```

<210> SEQ ID NO 58
<211> LENGTH: 127
<212> TYPE: PRT
<213> ORGANISM: Artificial Sequence
<220> FEATURE:
<223> OTHER INFORMATION: Synthetic

<400> SEQUENCE: 58

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn His
            20                  25                  30
Trp Met Thr Trp Val Arg Gln Thr Pro Gly Lys Gly Leu Glu Trp Val
```

```
            35                  40                  45
Ala Ala Ile Asn Glu Asp Gly Ser Glu Lys Tyr Tyr Val Gly Ser Val
        50                  55                  60
Lys Val Arg Phe Thr Ile Ser Arg Asp Asn Ala Lys Asn Ser Leu Tyr
65                  70                  75                  80
Leu Gln Met Asn Ser Leu Arg Val Glu Asp Thr Ala Val Tyr Tyr Cys
                85                  90                  95
Ala Arg Asp Tyr Tyr Asp Ile Leu Thr Asp Tyr Tyr Ile His Tyr Trp
                100                 105                 110
Tyr Phe Asp Leu Trp Gly Arg Gly Thr Leu Val Thr Val Ser Ser
                115                 120                 125

<210> SEQ ID NO 59
<211> LENGTH: 127
<212> TYPE: PRT
<213> ORGANISM: Artificial Sequence
<220> FEATURE:
<223> OTHER INFORMATION: Synthetic

<400> SEQUENCE: 59

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn His
                20                  25                  30
Trp Met Asn Trp Val Arg Gln Thr Pro Gly Lys Gly Leu Glu Trp Val
            35                  40                  45
Ala Ala Ile Asn Glu Asp Gly Ser Glu Lys Tyr Tyr Val Gly Ser Val
        50                  55                  60
Lys Val Arg Phe Ile Ile Ser Arg Asp Asn Ala Lys Asn Ser Leu Tyr
65                  70                  75                  80
Leu Gln Met Asn Ser Leu Arg Val Glu Asp Thr Ala Val Tyr Tyr Cys
                85                  90                  95
Thr Arg Asp Tyr Tyr Asp Ile Leu Thr Asp Tyr Tyr Ile His Tyr Trp
                100                 105                 110
Tyr Phe Asp Leu Trp Gly Arg Gly Thr Leu Val Thr Val Ser Ser
                115                 120                 125

<210> SEQ ID NO 60
<211> LENGTH: 127
<212> TYPE: PRT
<213> ORGANISM: Artificial Sequence
<220> FEATURE:
<223> OTHER INFORMATION: Synthetic

<400> SEQUENCE: 60

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn His
                20                  25                  30
Trp Met Asn Trp Val Arg Gln Thr Pro Gly Lys Gly Leu Glu Trp Val
            35                  40                  45
Ala Ala Ile Asn Glu Asp Gly Ser Glu Lys Tyr Tyr Val Gly Ser Val
        50                  55                  60
Lys Val Arg Phe Thr Ile Ser Arg Asp Asn Ala Lys Asn Ser Val Tyr
65                  70                  75                  80
Leu Gln Met Asn Ser Leu Arg Val Glu Asp Thr Ala Val Tyr Tyr Cys
                85                  90                  95
```

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 61
<211> LENGTH: 127
<212> TYPE: PRT
<213> ORGANISM: Artificial Sequence
<220> FEATURE:
<223> OTHER INFORMATION: Synthetic

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Ile Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 62
<211> LENGTH: 126
<212> TYPE: PRT
<213> ORGANISM: Artificial Sequence
<220> FEATURE:
<223> OTHER INFORMATION: Synthetic

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Thr Arg Asp Tyr Tyr Asp Ile Leu Thr Asp Tyr Ile His Tyr Trp Tyr
            100                 105                 110

Phe Asp Leu Trp Gly Arg Gly Thr Leu Val Thr Val Ser Ser
        115                 120                 125

<210> SEQ ID NO 63
<211> LENGTH: 127
<212> TYPE: PRT
<213> ORGANISM: Artificial Sequence -continued
<220> FEATURE:
<223> OTHER INFORMATION: Synthetic

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Ile Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Thr Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 64
<211> LENGTH: 127
<212> TYPE: PRT
<213> ORGANISM: Artificial Sequence
<220> FEATURE:
<223> OTHER INFORMATION: Synthetic

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Asp Trp Val Arg Gln Thr Pro Gly Lys Gly Leu Glu Trp Val
        35                  40                  45

Ala Ser Ile Lys Glu Asp Gly Ser Glu Lys Tyr Tyr Val Asp Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 65
<211> LENGTH: 127
<212> TYPE: PRT
<213> ORGANISM: Artificial Sequence
<220> FEATURE:
<223> OTHER INFORMATION: Synthetic

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Asp Phe
            20                  25                  30

Trp Met Asp Trp Val Arg Gln Thr Pro Gly Lys Gly Leu Glu Trp Val
            35                  40                  45

Ala Asn Ile Lys Glu Asp Gly Ser Glu Lys Tyr Tyr Val Asp Ser Val
 50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
             100                 105                 110

Tyr Phe Asp Leu Trp Gly Arg Gly Thr Leu Val Thr Val Ser Ser
             115                 120                 125

<210> SEQ ID NO 66
<211> LENGTH: 127
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Phe
                 20                  25                  30

Trp Met Asp Trp Val Arg Gln Thr Pro Gly Lys Gly Leu Glu Trp Val
            35                  40                  45

Ala Ser Ile Lys Glu Asp Gly Ser Glu Lys Tyr Tyr Val Asp Ser Val
 50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Asp Tyr Tyr Asp Ile Leu Thr Asp Tyr Tyr Ile His Tyr Trp
             100                 105                 110

Tyr Phe Asp Leu Trp Gly Arg Gly Thr Leu Val Thr Val Ser Ser
             115                 120                 125

<210> SEQ ID NO 67
<211> LENGTH: 127
<212> TYPE: PRT
<213> ORGANISM: Artificial Sequence
<220> FEATURE:
<223> OTHER INFORMATION: Synthetic

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Phe
                 20                  25                  30

Trp Met Asp Trp Val Arg Gln Thr Pro Gly Lys Gly Leu Glu Trp Val
            35                  40                  45

Ala Ser Ile Lys Glu Asp Gly Ser Glu Lys Tyr Tyr Val Gly Ser Val
 50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

```
Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 68
<211> LENGTH: 127
<212> TYPE: PRT
<213> ORGANISM: Artificial Sequence
<220> FEATURE:
<223> OTHER INFORMATION: Synthetic

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Asp Trp Val Arg Gln Thr Pro Gly Lys Gly Leu Glu Trp Val
        35                  40                  45

Ala Ser Ile Lys Glu Asp Gly Ser Glu Lys Tyr Tyr Val Gly Ser Val
    50                  55                  60

Lys Val Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
            85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 69
<211> LENGTH: 127
<212> TYPE: PRT
<213> ORGANISM: Artificial Sequence
<220> FEATURE:
<223> OTHER INFORMATION: Synthetic

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Asp Trp Val Arg Gln Thr Pro Gly Lys Gly Leu Glu Trp Val
        35                  40                  45

Ala Ser Ile Lys Glu Asp Gly Ser Glu Lys Tyr Tyr Val Gly Ser Val
    50                  55                  60

Lys Val Arg Phe Ile Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
            85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 70
<211> LENGTH: 127
<212> TYPE: PRT
```

```
<213> ORGANISM: Artificial Sequence
<220> FEATURE:
<223> OTHER INFORMATION: Synthetic

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Asp Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
            85                  90                  95

Val Arg Asp Tyr Tyr Asp Ile Leu Thr Asp Tyr Tyr Ile His Tyr Trp
        100                 105                 110

Tyr Phe Asp Leu Trp Gly Arg Gly Thr Leu Val Thr Val Ser Ser
        115                 120                 125

<210> SEQ ID NO 71
<211> LENGTH: 127
<212> TYPE: PRT
<213> ORGANISM: Artificial Sequence
<220> FEATURE:
<223> OTHER INFORMATION: Synthetic

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Asp Trp Val Arg Gln Thr Pro Gly Lys Gly Leu Glu Trp Val
        35                  40                  45

Ala Ser Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
            85                  90                  95

Val Arg Asp Tyr Tyr Asp Ile Leu Thr Asp Tyr Tyr Ile His Tyr Trp
        100                 105                 110

Tyr Phe Asp Leu Trp Gly Arg Gly Thr Leu Val Thr Val Ser Ser
        115                 120                 125

<210> SEQ ID NO 72
<211> LENGTH: 127
<212> TYPE: PRT
<213> ORGANISM: Artificial Sequence
<220> FEATURE:
<223> OTHER INFORMATION: Synthetic

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30
```

```
Trp Met Asp Trp Val Arg Gln Thr Pro Gly Lys Gly Leu Glu Trp Val
            35                  40                  45

Ala Ser Ile Asn Glu Asp Gly Ser Glu Lys Tyr Tyr Val Gly Ser Val
        50                  55                  60

Lys Val Arg Phe Ile Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
                115                 120                 125

<210> SEQ ID NO 73
<211> LENGTH: 127
<212> TYPE: PRT
<213> ORGANISM: Artificial Sequence
<220> FEATURE:
<223> OTHER INFORMATION: Synthetic

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Phe Glu Ile Val Thr Asn Tyr Phe Val His Tyr Trp
                100                 105                 110

Tyr Phe Glu Leu Trp Gly Arg Gly Thr Leu Val Thr Val Ser Ser
                115                 120                 125

<210> SEQ ID NO 74
<211> LENGTH: 127
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Ala Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                    85                  90                  95
Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 75
<211> LENGTH: 127
<212> TYPE: PRT
<213> ORGANISM: Artificial Sequence
<220> FEATURE:
<223> OTHER INFORMATION: Synthetic

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ile Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 76
<211> LENGTH: 127
<212> TYPE: PRT
<213> ORGANISM: Artificial Sequence
<220> FEATURE:
<223> OTHER INFORMATION: Synthetic

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Val
        35                  40                  45

Ala Ser Ile Arg Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 77
<211> LENGTH: 127
```

<212> TYPE: PRT
<213> ORGANISM: Artificial Sequence
<220> FEATURE:
<223> OTHER INFORMATION: Synthetic

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Ala Pro Gly Lys Gly Leu Glu Trp Val
        35                  40                  45

Ala Gly Ile Arg Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 78
<211> LENGTH: 135
<212> TYPE: PRT
<213> ORGANISM: Artificial Sequence
<220> FEATURE:
<223> OTHER INFORMATION: Synthetic

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
            85                  90                  95

Ala Arg Asp Tyr Tyr Asp Ile Leu Thr Arg Asp Tyr Tyr Asp Ile Leu
            100                 105                 110

Thr Asp Tyr Tyr Ile His Tyr Trp Tyr Phe Asp Leu Trp Gly Arg Gly
            115                 120                 125

Thr Leu Val Thr Val Ser Ser
    130                 135

<210> SEQ ID NO 79
<211> LENGTH: 135
<212> TYPE: PRT
<213> ORGANISM: Artificial Sequence
<220> FEATURE:
<223> OTHER INFORMATION: Synthetic

<400> SEQUENCE: 79

Glu Val Gln Leu Val Glu Ser Gly Gly Gly Leu Val Gln Pro Gly Gly

```
            1               5                   10                  15
Ser Leu Arg Leu Ser Cys Ala Ala Ser Gly Phe Thr Phe Ser Asn His
                20                  25                  30

Trp Met Asn Trp Val Arg Gln Thr Pro Gly Lys Gly Leu Glu Trp Val
                35                  40                  45

Ala Ala Ile Asn Glu Asp Gly Ser Glu Lys Tyr Tyr Val Gly Ser Val
            50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Arg Asp Tyr Tyr Asp Ile Leu
                100                 105                 110

Thr Asp Tyr Tyr Ile His Tyr Trp Tyr Phe Asp Leu Trp Gly Arg Gly
                115                 120                 125

Thr Leu Val Thr Val Ser Ser
            130                 135

<210> SEQ ID NO 80
<211> LENGTH: 109
<212> TYPE: PRT
<213> ORGANISM: Artificial Sequence
<220> FEATURE:
<223> OTHER INFORMATION: Synthetic

<400> SEQUENCE: 80

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Asp Ile Lys Arg
            100                 105

<210> SEQ ID NO 81
<211> LENGTH: 109
<212> TYPE: PRT
<213> ORGANISM: Artificial Sequence
<220> FEATURE:
<223> OTHER INFORMATION: Synthetic

<400> SEQUENCE: 81

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
            50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Leu Thr Phe Gly Gly Gly Thr Lys Val Glu Ile Lys Arg
            100                 105
```

<210> SEQ ID NO 82
<211> LENGTH: 422
<212> TYPE: PRT
<213> ORGANISM: Artificial Sequence
<220> FEATURE:
<223> OTHER INFORMATION: Synthetic

<400> SEQUENCE: 82

```
Met Arg Ala Trp Ile Phe Phe Leu Leu Cys Leu Ala Gly Arg Ala Leu
  1               5                  10                  15

Ala His His His His His Glu Gln Lys Leu Ile Ser Glu Glu Asp
                 20                  25                  30

Leu Gly Gly Ser Gly Gly Met Val Ser Lys Gly Glu Thr Thr Met
             35                  40                  45

Gly Val Ile Lys Pro Asp Met Lys Ile Lys Leu Lys Met Glu Gly Asn
 50                  55                  60

Val Asn Gly His Ala Phe Val Ile Glu Gly Glu Gly Glu Gly Lys Pro
 65                  70                  75                  80

Tyr Asp Gly Thr Asn Thr Ile Asn Leu Glu Val Lys Glu Gly Ala Pro
                 85                  90                  95

Leu Pro Phe Ser Tyr Asp Ile Leu Thr Thr Ala Phe Ser Tyr Gly Asn
                100                 105                 110

Arg Ala Phe Thr Lys Tyr Pro Asp Asp Ile Pro Asn Tyr Phe Lys Gln
                115                 120                 125

Ser Phe Pro Glu Gly Tyr Ser Trp Glu Arg Thr Met Thr Phe Glu Asp
            130                 135                 140

Lys Gly Ile Val Lys Val Lys Ser Asp Ile Ser Met Glu Glu Asp Ser
145                 150                 155                 160

Phe Ile Tyr Glu Ile His Leu Lys Gly Glu Asn Phe Pro Pro Asn Gly
                165                 170                 175

Pro Val Met Gln Lys Glu Thr Thr Gly Trp Asp Ala Ser Thr Glu Arg
                180                 185                 190

Met Tyr Val Arg Asp Gly Val Leu Lys Gly Asp Val Lys Met Lys Leu
            195                 200                 205

Leu Leu Glu Gly Gly Gly His His Arg Val Asp Phe Lys Thr Ile Tyr
210                 215                 220

Arg Ala Lys Lys Ala Val Lys Leu Pro Asp Tyr His Phe Val Asp His
225                 230                 235                 240

Arg Ile Glu Ile Leu Asn His Asp Lys Asp Tyr Asn Lys Val Thr Val
                245                 250                 255

Tyr Glu Ile Ala Val Ala Arg Asn Ser Thr Asp Gly Met Asp Glu Leu
                260                 265                 270

Tyr Lys Ala Gly Gly Ala Ser Gly Ala Gly Ser Gly Ser Gly Ala
            275                 280                 285

Ser Gly Gly Ile Thr Ile Pro Arg Asn Pro Gly Cys Pro Asn Ser Glu
            290                 295                 300

Asp Lys Asn Phe Pro Arg Thr Val Met Val Asn Leu Asn Ile His Asn
305                 310                 315                 320
```

-continued

Arg Asn Thr Asn Thr Asn Pro Lys Arg Ser Asp Tyr Tyr Asn Arg
            325                 330                 335

Ser Thr Ser Pro Trp Asn Leu His Arg Asn Glu Asp Pro Glu Arg Tyr
        340                 345                 350

Pro Ser Val Ile Trp Glu Ala Lys Cys Arg His Leu Gly Cys Ile Asn
        355                 360                 365

Ala Asp Gly Asn Val Asp Tyr His Met Asn Ser Val Pro Ile Gln Gln
        370                 375                 380

Glu Ile Leu Val Leu Arg Arg Glu Pro Pro His Cys Pro Asn Ser Phe
385                 390                 395                 400

Arg Leu Glu Lys Ile Leu Val Ser Val Gly Cys Thr Cys Val Thr Pro
                405                 410                 415

Ile Val His His Val Ala
            420

<210> SEQ ID NO 83
<211> LENGTH: 127
<212> TYPE: PRT
<213> ORGANISM: Artificial Sequence
<220> FEATURE:
<223> OTHER INFORMATION: Synthetic

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn His
            20                  25                  30

Trp Met Asn Trp Val Arg Gln Thr Pro Gly Lys Gly Leu Glu Trp Val
        35                  40                  45

Ala Ala Ile Asn Glu Asp Gly Ser Glu Lys Tyr Tyr Val Gly Ser Val
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 84
<211> LENGTH: 127
<212> TYPE: PRT
<213> ORGANISM: Artificial Sequence
<220> FEATURE:
<223> OTHER INFORMATION: Synthetic

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 85
<211> LENGTH: 127
<212> TYPE: PRT
<213> ORGANISM: Artificial Sequence
<220> FEATURE:
<223> OTHER INFORMATION: Synthetic

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Lys Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 86
<211> LENGTH: 127
<212> TYPE: PRT
<213> ORGANISM: Artificial Sequence
<220> FEATURE:
<223> OTHER INFORMATION: Synthetic

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Lys Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 87
```

<211> LENGTH: 127
<212> TYPE: PRT
<213> ORGANISM: Artificial Sequence
<220> FEATURE:
<223> OTHER INFORMATION: Synthetic

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

<210> SEQ ID NO 88
<211> LENGTH: 127
<212> TYPE: PRT
<213> ORGANISM: Artificial Sequence
<220> FEATURE:
<223> OTHER INFORMATION: Synthetic

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

<210> SEQ ID NO 89
<211> LENGTH: 127
<212> TYPE: PRT
<213> ORGANISM: Artificial Sequence
<220> FEATURE:
<223> OTHER INFORMATION: Synthetic

<400> SEQUENCE: 89

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 90
<211> LENGTH: 127
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ala Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 91
<211> LENGTH: 127
<212> TYPE: PRT
<213> ORGANISM: Artificial Sequence
<220> FEATURE:
<223> OTHER INFORMATION: Synthetic

<400> SEQUENCE: 91

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ala Ile Lys Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
 65                 70                  75                  80
```

Leu Gln Met Asn Ser Leu Arg Ala Glu Asp Thr Ala Val Tyr Tyr Cys
                    85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 92
<211> LENGTH: 127
<212> TYPE: PRT
<213> ORGANISM: Artificial Sequence
<220> FEATURE:
<223> OTHER INFORMATION: Synthetic

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 93
<211> LENGTH: 127
<212> TYPE: PRT
<213> ORGANISM: Artificial Sequence
<220> FEATURE:
<223> OTHER INFORMATION: Synthetic

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Ala Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser
            115                 120                 125

<210> SEQ ID NO 94
<211> LENGTH: 127
<212> TYPE: PRT
<213> ORGANISM: Artificial Sequence
<220> FEATURE:
<223> OTHER INFORMATION: Synthetic

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 95
<211> LENGTH: 127
<212> TYPE: PRT
<213> ORGANISM: Artificial Sequence
<220> FEATURE:
<223> OTHER INFORMATION: Synthetic

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 96
<211> LENGTH: 127
<212> TYPE: PRT
<213> ORGANISM: Artificial Sequence
<220> FEATURE:
<223> OTHER INFORMATION: Synthetic

<400> SEQUENCE: 96

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Ala Ile Lys Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 97
<211> LENGTH: 127
<212> TYPE: PRT
<213> ORGANISM: Artificial Sequence
<220> FEATURE:
<223> OTHER INFORMATION: Synthetic

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ala Ile Lys Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
            115                 120                 125

<210> SEQ ID NO 98
<211> LENGTH: 127
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Lys Tyr Tyr Val Gly Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

<210> SEQ ID NO 99
<211> LENGTH: 127
<212> TYPE: PRT
<213> ORGANISM: Artificial Sequence
<220> FEATURE:
<223> OTHER INFORMATION: Synthetic

<400> SEQUENCE: 99

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met Ser Trp Val Arg Gln Ala Pro Gly Lys Gly Leu Glu Trp Val
             35                  40                  45

Ala Ala Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

<210> SEQ ID NO 100
<211> LENGTH: 127
<212> TYPE: PRT
<213> ORGANISM: Artificial Sequence
<220> FEATURE:
<223> OTHER INFORMATION: Synthetic

<400> SEQUENCE: 100

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met Asn Trp Val Arg Gln Ala Pro Gly Lys Gly Leu Glu Trp Val
             35                  40                  45

Ala Ala Ile Lys Gln Asp Gly Ser Glu Lys Tyr Tyr Val Gly Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

US 9,328,166 B2

ANTIBODIES DIRECTED AGAINST IL-17

CROSS-REFERENCE TO RELATED APPLICATIONS

This patent application claims the benefit of U.S. Provisional Patent Application No. 61/370,978, filed Aug. 5, 2010, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 119,461 Byte ASCII (Text) file named "712061_ST25.TXT," created on Feb. 4, 2013.

BACKGROUND OF THE INVENTION

Interleukin-17 (IL-17) is a pro-inflammatory cytokine secreted by activated T-cells. The IL-17 family of cytokines includes IL-17B, IL-17C, IL-17D, IL-17E (also called IL-25), and IL-17F, and the prototype member of the family has been designated IL-17A (see, e.g., Moseley et al., *Cytokine Growth Factor Rev.*, 14(2): 155-74 (2003)). All members of the IL-17 family have a similar protein structure, with four highly conserved cysteine residues critical to their three-dimensional shape, yet they have no sequence similarity to any other known cytokines. However, a viral homologue of IL-17A has been found in open reading frame 13 of *Herpesvirus saimiri* (see, e.g., Yao et al., *Immunity*, 3: 811 (1995)), which has 72% amino acid residue identity to human IL-17A.

Multiple functions have been reported for the IL-17 family members, which primarily involve regulation of the immune response. For example, IL-17 is involved in upregulating adhesion molecules and inducing the production of multiple inflammatory cytokines and chemokines from various cell types, including synoviocytes, chondrocytes, fibroblasts, endothelial cells, epithelial cells, keratinocytes, and macrophages. Also, IL-17 induces recruitment of neutrophils to an inflammatory site through induction of chemokine release, stimulates production of prostaglandins and metalloproteinases, and inhibits proteoglycan synthesis. IL-17 plays an important role in the maturation of hematopoietic progenitor cells, and IL-17 appears to have signaling roles in different organs and tissues including lung, articular cartilage, bone, brain, hematopoietic cells, kidney, skin, and intestine (see, e.g., Kolls and Linden, *Immunity*, 21: 467-476 (2004), and Fossiez, et al., *Int. Rev. Immunol.*, 16: 541 (1998)). IL-17 also induces matrix metalloproteinases (MMP) production and downregulates tissue inhibitor of metalloproteinases (TIMPs) (see, e.g., Jovanovic et al., *J. Rheumatol.*, 28: 712-718 (2001)), and blockage of IL-1 and IL-17 has a synergistic effect on inflammation and bone destruction in vivo (see, e.g., Chabaud et al., *Arthritis Rheum.*, 44: 1293-1303 (2001)).

Inappropriate or increased production of IL-17 (i.e., IL-17A) has been associated with several diseases, such as airway inflammation, asthma, rheumatoid arthritis (RA), osteoarthritis, osteoporosis, bone erosion, intraperitoneal abscesses and adhesions, inflammatory bowel disorder (IBD), chronic obstructive pulmonary disorder (COPD), Addison's disease, agammaglobulinemia, allergic asthma, alopecia greata, Celiac spruce, Chagas disease, idiopathic pulmonary fibrosis, Crohn's disease, ulcerative colitis, allograft rejection (e.g., renal), psoriatic arthritis, uveitis, Behcet's disease, certain types of cancer, angiogenesis, atherosclerosis, multiple sclerosis (MS), systemic lupus erythematosus, septicemia, septic or endotoxic shock, response to allergen exposure, *Helicobacter pylori*-associated gastritis, bronchial asthma, ankylosing spondylitis, lupus nephritis, psoriasis, ischemia, systemic sclerosis, stroke, and other inflammatory disorders (see, e.g., Witowski et al., *Cell Mol. Life. Sci.*, 61: 567-579 (2004); Antonysamy et al., *J. Immunol.*, 162: 577-584 (1999), van Kooten et al., *J. Am. Soc. Nephrol.*, 9: 1526-1534 (1998); Molet et al., *J. Allergy Clin. Immunol.*, 108: 430-438 (2001); Teunissen et al., *J. Invest. Dermatol.*, 111: 645-649 (1998); and Kurasawa et al., *Arthritis Rheum.*, 43: 2455-2463 (2000)).

Based on the foregoing, IL-17 appears to be a target for the treatment of several inflammatory or autoimmune diseases. To this end, antibodies that bind IL-17 have been proposed for use in treating IL-17-mediated diseases and disorders (see, e.g., International Patent Application Publication Nos. WO 2006/013107 and WO 2007/117749; and U.S. Patent Application Publication Nos. 2008/0269467 A1 and 2009/0280131 A1). In addition, blocking of IL-17 bioactivity by an IL-17-specific antibody or soluble receptor binding to IL-17 reduces inflammation and bone erosion in various animal arthritis models (see, e.g., Lubberts et al., *Arthritis & Rheumatism*, 50: 650-659 (2004)). However, the therapeutic utility of currently available IL-17 antibodies is limited by their sub-optimum pharmacokinetics, stability and efficacy in vivo.

Therefore, there is a need for an IL-17-binding agent (e.g., an antibody) which binds IL-17 with a high affinity, exhibits increased stability and improved pharmacokinetics, and effectively neutralizes IL-17 activity in vivo. The invention provides such an IL-17 binding agent.

BRIEF SUMMARY OF THE INVENTION

The invention provides an isolated IL-17-binding agent which comprises one or both of the following: (a) an immunoglobulin heavy chain polypeptide comprising SEQ ID NO: 1 except that one or more of residues 32, 53, and 59 of SEQ ID NO: 1 are replaced with a different residue, and optionally one or more of residues 30, 31, 35, 40, 50, 52, 53, 59, 62, 66, 69, 75, 79, 88, and 97 of SEQ ID NO: 1 are replaced with a different residue, or a fragment thereof comprising at least five amino acids, and (b) an immunoglobulin light chain polypeptide comprising SEQ ID NO: 23, except that one or more of residues 9, 10, 11, 13, 17, 20, 21, and 22 of SEQ ID NO: 23 are replaced with a different residue, or an amino acid sequence that is at least 85% identical thereto.

The invention also provides an isolated IL-17-binding agent comprising an immunoglobulin heavy chain polypeptide comprising the amino acid sequence SEQ ID NO: 1 except that the residue at position 50 of SEQ ID NO: 1 is replaced with an S, A, or I residue, and optionally one or more of residues 31, 32, 35, 40, 52, 62, 66, 88, and 97 of SEQ ID NO: 1 are replaced with a different residue, or an amino acid sequence that is at least 85% identical thereto.

The invention further provides an isolated IL-17-binding agent comprising an immunoglobulin heavy chain polypeptide comprising the amino acid sequence of SEQ ID NO: 1 except that one or more of residues 104, 109, and 115 of SEQ ID NO: 1 are replaced with a different residue, and optionally one or more of residues 100, 101, 102, 106, 107, 108, and 111 of SEQ ID NO: 1 are replaced with a different residue, or an amino acid sequence that is at least 85% identical thereto.

The invention provides an isolated IL-17-binding agent comprising an immunoglobulin heavy chain polypeptide comprising the amino acid sequence SEQ ID NO: 32, SEQ ID NO: 33, SEQ ID NO: 78, or SEQ ID NO: 79, or an amino acid sequence that is at least 85% identical thereto.

BRIEF DESCRIPTION OF THE SEVERAL VIEWS OF THE DRAWING(S)

DETAILED DESCRIPTION OF THE INVENTION

Figure 1:
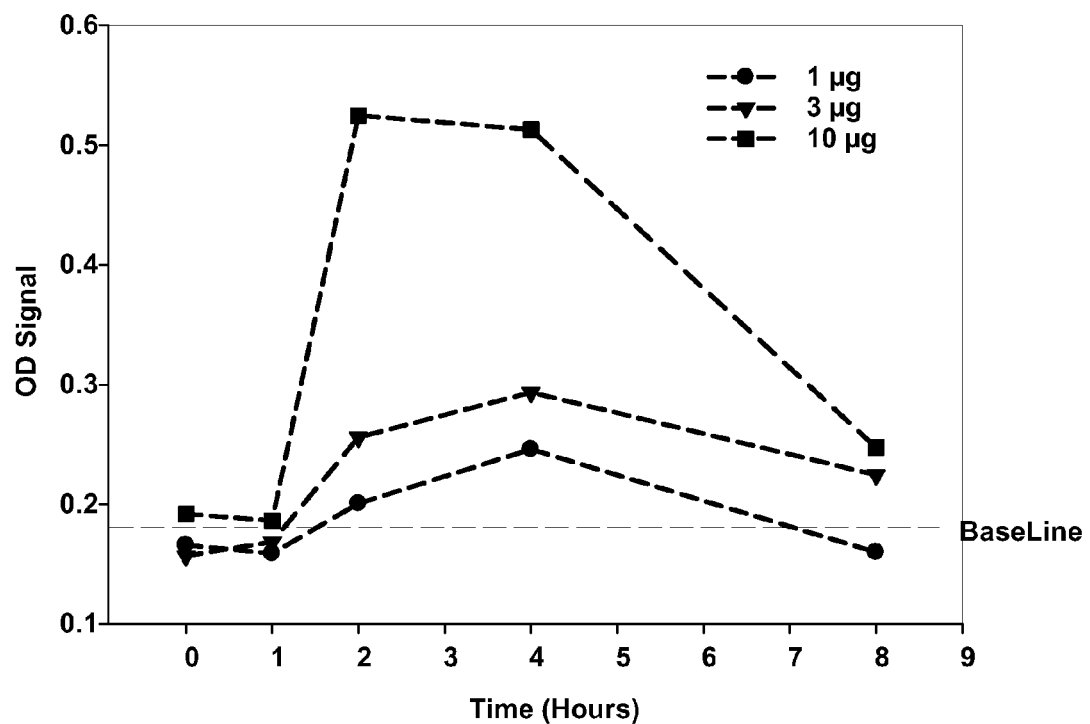
FIG. 1 is a graph illustrating changes in the KC(CXCL1) profile vs. time following subcutaneous hIL-17 administration at 1, 3, and 10 µg dose/mouse.

The invention provides an isolated IL-17-binding agent which comprises an immunoglobulin heavy chain polypeptide and/or an isolated immunoglobulin light chain polypeptide, or a fragment (e.g., immunogenic fragment) thereof. By "IL-17-binding agent" is meant a molecule, preferably a proteinaceous molecule, that specifically binds to the cytokine IL-17. Preferably, the IL-17-binding agent is an antibody or a fragment (e.g., immunogenic fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($CH_1$, $CH_2$ and $CH_3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding. The four framework regions (FWs or FRs) largely adopt a beta-sheet conformation, and the CDRs form loops connecting, and in some cases comprising part of, the beta-sheet structure. The constant regions of the light and heavy chains are not directly involved in binding of the antibody to an antigen, but exhibit various effector functions, such as participation in antibody-dependent cellular toxicity via interactions with effector molecules and cells.

The IL-17-binding agent of the invention desirably binds to interleukin-17 (IL-17, or IL-17A). IL-17A is the founding member of a group of cytokines called the IL-17 family. IL-17A was originally identified as a transcript from a rodent T-cell hybridoma, and is known as CTLA8 in rodents (Rouvier et al., *J. Immunol.*, 150 (12): 5445-5456 (1993)). IL-17A binds to a type I cell surface receptor called IL-17R, of which there are at least three variants IL17RA, IL17RB, and IL17RC (Starnes et al., *J. Immunol.*, 169 (2): 642-646 (2002)). In addition to IL-17A, the IL-17 family includes the cytokines IL-17B, IL-17C, IL-17D, IL-17E (also called IL-25), and IL-17F. All members of the IL-17 family have a similar protein structure, with four highly conserved cysteine residues critical to their 3-dimensional shape, yet they have no sequence similarity to any other known cytokines.

As discussed above, the members of the IL-17 protein family exhibit numerous immune regulatory functions, which are primarily due to their ability to induce immune signaling molecules. In particular, IL-17 has been shown to induce and mediate proinflammatory responses, and is commonly associated with allergic responses. IL-17 induces the production of cytokines, such as IL-6, G-CSF, GM-CSF, IL-1β, TGF-β, TNF-α, chemokines (e.g., IL-8, GRO-α, and MCP-1), and prostaglandins (e.g., PGE2) from many cell types (e.g., fibroblasts, endothelial cells, epithelial cells, keratinocytes, and macrophages). The release of cytokines causes many functions, such as airway remodeling, which is a characteristic of IL-17 responses. The increased expression of chemokines attracts other cells including neutrophils but not eosinophils. IL-17 function is also essential to a subset of CD4+ T-cells called T helper 17 (Th17) cells. As such, the IL-17 family of proteins has been associated with the pathology of several immune and autoimmune related diseases, including, but not limited to, rheumatoid arthritis, asthma, lupus, allograft rejection, and anti-tumor immunity (see, e.g., Aggarwal et al., *J. Leukoc. Biol.*, 71 (1): 1-8 (2002)). The IL-17-binding agent of the invention can bind any member of the of the IL-17 protein family described herein, such as, e.g., IL-17A and/or IL-17F. In a preferred embodiment, the IL-17-binding agent binds to the IL-17A protein. In another embodiment, the IL-17-binding agent can bind to, or cross-react with, human and/or non-human orthologs of IL-17A.

The isolated IL-17-binding agent of the invention comprises an immunoglobulin heavy chain polypeptide, or a fragment thereof comprising at least five amino acids, and/or an immunoglobulin light chain polypeptide, or a fragment thereof comprising at least five amino acids. In one embodiment, the isolated IL-17-binding agent comprises the immunoglobulin heavy chain polypeptide or the immunoglobulin light chain polypeptide. In another embodiment, the isolated IL-17-binding agent comprises both the immunoglobulin heavy chain polypeptide and the immunoglobulin light chain polypeptide. The amino acid sequence of several immunoglobulin heavy chain and light chain polypeptides which bind one or more members of the IL-17 protein family are known in the art (see, e.g., International Patent Application Publication Nos. WO 2006/013107 and WO 2007/117749; and U.S. Patent Application Publication Nos. 2008/0269467 A1 and 2009/0280131 A1).

One example of an immunoglobulin heavy chain polypeptide that binds to IL-17 comprises SEQ ID NO: 1, or an amino acid sequence that is at least 85% identical thereto (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical thereto). In the context of the invention, the immunoglobulin heavy chain polypeptide comprises SEQ ID NO: 1 except that one or more of residues of SEQ ID NO: 1 are replaced with a different amino acid residue. In this respect, one or more of residues 32, 53, and 59 of SEQ ID NO: 1 are replaced with a different residue, and optionally one or more of residues 30, 31, 35, 40, 50, 52, 53, 59, 62, 66, 69, 75, 79, 88, and 97 of SEQ ID NO: 1 are replaced with a different residue. Each of amino acid residues 30, 31, 35, 40, 50, 52, 53, 59, 62, 66, 69, 75, 79, 88, and 97 of SEQ ID NO: 1 can be replaced with any suitable amino acid residue that can be the same or different in each position. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz, G. E. and R. H. Schirmer, supra).

Examples of conservative amino acid substitutions include substitutions of amino acids within the sub-groups above, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH$_2$ can be maintained.

"Semi-conservative mutations" include amino acid substitutions of amino acids with the same groups listed above, that do not share the same sub-group. For example, the mutation of aspartic acid for asparagine, or asparagine for lysine each involves amino acids within the same group, but different sub-groups. "Non-conservative mutations" involve amino acid substitutions between different groups, for example, lysine for tryptophan, or phenylalanine for serine, etc.

In one embodiment, the isolated IL-17-binding agent comprises an immunoglobulin heavy chain polypeptide which comprises SEQ ID NO: 1, except that residue 32 of SEQ ID NO: 1 is replaced with an H (histidine), S (serine), or F (phenylalanine) residue, residue 53 of SEQ ID NO: 1 is replaced with an E (glutamic acid) or H (histidine) residue, residue 59 of SEQ ID NO: 1 is replaced with an H (histidine) residue, or any combination of the foregoing replacements.

In addition to the amino acid substitutions discussed above, the immunoglobulin heavy chain polypeptide optionally can comprise additional amino acid substitutions. In one embodiment, the immunoglobulin heavy chain polypeptide comprises SEQ ID NO: 1, except that one or more of residues 30, 31, 35, 40, 50, 52, 53, 59, 62, 66, 69, 75, 79, 88, and 97 of SEQ ID NO: 1 are replaced with a different residue. In another embodiment, the immunoglobulin heavy chain polypeptide comprises SEQ ID NO: 1, except that residue 30 of SEQ ID NO: 1 is replaced with an N (asparagine) residue, residue 31 of SEQ ID NO: 1 is replaced with an N (asparagine) or D (aspartic acid) residue, residue 35 of SEQ ID NO: 1 is replaced with a T (threonine), N (asparagine), or D (aspartic acid) residue, residue 40 of SEQ ID NO: 1 is replaced with a T (threonine) residue, residue 50 of SEQ ID NO: 1 is replaced with an A (alanine), S (serine), I (isoleucine), or G (glycine) residue, residue 52 of SEQ ID NO: 1 is replaced with an N (asparagine) or R (arginine) residue, residue 53 of SEQ ID NO: 1 is replaced with an E (glutamic acid) or H (histidine) residue, residue 59 of SEQ ID NO: 1 is replaced with an H (histidine) residue, residue 62 of SEQ ID NO: 1 is replaced with a G (glycine) residue, residue 66 of SEQ ID NO: 1 is replaced with a V (valine) residue, residue 69 of SEQ ID NO: 1 is replaced with an I (isoleucine) residue, residue 75 of SEQ ID NO: 1 is replaced with a D (aspartic acid) residue, residue 79 of SEQ ID NO: 1 is replaced with a V (valine) residue, residue 88 of SEQ ID NO: 1 is replaced with a V (valine) residue, residue 97 of SEQ ID NO: 1 is replaced with a V (valine), T (threonine), L (leucine), or F (phenylalanine) residue, or any combination of the foregoing replacements.

Exemplary immunoglobulin heavy chain polypeptides can comprise any one of the following amino acid sequences: SEQ ID NO: 2, SEQ ID NO: 3-5, SEQ ID NO: 7, SEQ ID NO: 8, SEQ ID NOs: 10-20, SEQ ID NOs: 35-72, SEQ ID NO: 76, and SEQ ID NO: 77.

The invention also provides an isolated IL-17-binding agent comprising an immunoglobulin heavy chain polypeptide comprising the amino acid sequence SEQ ID NO: 1 except that the residue at position 50 of SEQ ID NO: 1 is replaced with a different residue, and optionally one or more of residues 31, 32, 35, 40, 52, 62, 66, 88, and 97 of SEQ ID NO: 1 are replaced with a different residue. In this regard, the amino acid residue at positions 50, 31, 32, 35, 40, 52, 62, 66, 88, and 97 of SEQ ID NO: 1 can be replaced with any suitable amino acid residue as described herein. In one embodiment, the residue at position 50 of SEQ ID NO: 1 is replaced with an S, A, or I residue. In other embodiments, residue 31 of SEQ ID NO: 1 is replaced with an N or D residue, residue 35 of SEQ ID NO: 1 is replaced with an N, T, or D residue, residue 40 of SEQ ID NO: 1 is replaced with a T residue, residue 52 of SEQ ID NO: 1 is replaced with an N or R residue, residue 62 of SEQ ID NO: 1 is replaced with a G residue, residue 66 of SEQ ID NO: 1 is replaced with a V residue, residue 88 of SEQ ID NO: 1 is replaced with a V residue, residue 97 of SEQ ID NO: 1 is replaced with a V, T, L, or F residue, or any combination of the foregoing replacements. For example, the immunoglobulin heavy chain polypeptide can comprise any one of SEQ ID NO: 6, SEQ ID NO: 9, SEQ ID NO: 31, SEQ ID NO: 34, SEQ ID NO: 74, or SEQ ID NO: 75.

The invention further provides an isolated IL-17-binding agent comprising an immunoglobulin heavy chain polypeptide comprising the amino acid sequence SEQ ID NO: 1 except that one or more of residues 104, 109, and 115 of SEQ ID NO: 1 are replaced with a different residue, and optionally one or more of residues 100, 101, 102, 106, 107, 108, and 111 of SEQ ID NO: 1 are replaced with a different residue. In this regard, the amino acid residue at positions 100, 101, 102, 104, 106, 107, 108, 109, 111, and 115 of SEQ ID NO: 1 can be replaced with any suitable amino acid residue as described herein. In one embodiment, residue 104 of SEQ ID NO: 1 is replaced with a V residue, residue 109 of SEQ ID NO: 1 is replaced with a V residue, residue 115 of SEQ ID NO: 1 is replaced with an N or E residue, or any combination of the foregoing replacements. In other embodiments, residue 100 of SEQ ID NO: 1 is replaced with an H residue, residue 101 of SEQ ID NO: 1 is replaced with an H or F residue, residue 102 of SEQ ID NO: 1 is replaced with an E residue, residue 106 of SEQ ID NO: 1 is replaced with an N residue, residue 107 of SEQ ID NO: 1 is replaced with an S residue, residue 108 of SEQ ID NO: 1 is replaced with an H or F residue, residue 111 of SEQ ID NO: 1 is replaced with an S residue, or any combination of the foregoing replacements. For example, the immunoglobulin heavy chain polypeptide can comprise SEQ ID NO: 21, SEQ ID NO: 22, or SEQ ID NO: 73.

In another embodiment, the IL-17 binding agent can comprise an immunoglobulin heavy chain polypeptide comprising the amino acid sequence SEQ ID NO: 1 except that one or more amino acid residues are inserted into SEQ ID NO: 1. Any number of amino acid residues can be inserted into SEQ ID NO: 1. Preferably, at least one amino acid residue (e.g., 2 or more, 3 or more, 5 or more, or 8 or more amino acid residues), but less than 20 amino acid residues (e.g., 18 or less, 15 or less, 12 or less, or 10 or less amino acid residues) are inserted into SEQ ID NO: 1. Preferably, about 3 to about 20 amino acid residues (e.g., about 3-5 amino acid residues, about 5-10 amino acid residues, about 10-15 amino acid residues, or about 15-20 amino acid residues, or a range defined by any two of the foregoing values) are inserted into SEQ ID NO: 1. In a preferred embodiment, no more than 8 amino acid residues are inserted in to SEQ ID NO: 1. For example, the immunoglobulin heavy chain polypeptide can comprise SEQ ID NO: 78 or SEQ ID NO: 79.

One example of an immunoglobulin light chain polypeptide that is specific for IL-17 comprises SEQ ID NO: 23, or an amino acid sequence that is at least 85% identical thereto (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical thereto). In the context of the invention, the isolated IL-17-binding agent comprises an immunoglobulin light chain polypeptide which comprises SEQ ID NO: 23 except that one or more of residues of SEQ ID NO: 23 are replaced with a different amino acid residue. In this respect, one or more of residues 9, 10, 11, 13, 17, 20, 21, and 22 of SEQ ID NO: 23 are replaced with a different residue. Amino acid residues 9, 10, 11, 13, 17, 20, 21, and 22 of SEQ ID NO: 23 can be replaced with any suitable amino acid residue as described herein.

In one embodiment, the immunoglobulin light chain polypeptide comprises SEQ ID NO: 23, except that residue 9 of SEQ ID NO: 23 is replaced with a Y (tyrosine) residue, residue 10 of SEQ ID NO: 23 is replaced with an R (arginine) residue, residue 11 of SEQ ID NO: 23 is replaced with a T (threonine) residue, residue 13 of SEQ ID NO: 23 is replaced with an L (leucine) or I (isoleucine) residue, residue 17 of SEQ ID NO: 23 is replaced with a G (glycine) residue, residue 20 of SEQ ID NO: 23 is replaced with a K (lysine) residue, residue 21 of SEQ ID NO: 23 is replaced with a V (valine) residue, residue 22 of SEQ ID NO: 23 is replaced with a D (aspartic acid) residue, or any combination of the foregoing replacements. For example, the immunoglobulin light chain polypeptide can comprise the amino acid sequence of SEQ ID NO: 24, SEQ ID NO: 25, SEQ ID NO: 26, SEQ ID NO: 27, SEQ ID NO: 28, SEQ ID NO: 80, or SEQ ID NO: 81.

The invention is not limited to an isolated IL-17-binding agent comprising an immunoglobulin heavy chain polypeptide or light chain polypeptide having replacements of the specific amino acid residues disclosed herein. Indeed, any amino acid residue of SEQ ID NO: 1 or SEQ ID NO: 23 can be replaced, in any combination, with a different amino acid residue, or any number of amino acid residues can be inserted into SEQ ID NO: 1 or SEQ ID NO: 23, so long as the biological activity of the IL-17-binding agent is enhanced or improved as a result of the amino acid replacements or insertions. The "biological activity" of an IL-17-binding agent refers to, for example, binding affinity for a particular IL-17 epitope, neutralization of IL-17 activity in vivo (e.g., $IC_{50}$), in vivo stability (including but not limited to thermal stability and proteolytic stability), pharmacokinetics, the immunogenic properties of the IL-17-binding agent, and cross-reactivity (e.g., with non-human homologs or orthologs of IL-17, or with other proteins or tissues). Other biological properties or characteristics of an antigen-binding agent recognized in the art include, for example, avidity, selectivity, solubility, folding, immunotoxicity, expression, formulation, and catalytic activity. The aforementioned properties or characteristics can be observed, measured, and/or assessed using standard techniques including, but not limited to, ELISA, competitive ELISA, BIACORE or KINEXA surface plasmon resonance analysis, in vitro or in vivo neutralization assays, receptor binding assays, cytokine or growth factor production and/or secretion assays, and signal transduction and immunohistochemistry assays.

The terms "inhibit" or "neutralize," as used herein with respect to the activity of an IL-17-binding agent, refer to the ability to substantially antagonize, prohibit, prevent, restrain, slow, disrupt, eliminate, stop, or reverse the progression or severity of, for example, the biological activity of IL-17, or a disease or condition associated with IL-17. The isolated IL-17-binding agent of the invention preferably inhibits or neutralizes the activity of an IL-17 by at least about 20%, about 30%, about 40%, about 50%, about 60%, about 70%, about 80%, about 90%, about 95%, about 100%, or a range defined by any two of the foregoing values.

The isolated IL-17-binding agent of the invention can be a whole antibody, as described herein, or an antibody fragment. The terms "fragment of an antibody," "antibody fragment," or "functional fragment of an antibody" are used interchangeably herein to mean one or more fragments of an antibody that retain the ability to specifically bind to an antigen (see, generally, Holliger et al., *Nat. Biotech.*, 23(9): 1126-1129 (2005)). The isolated IL-17-binding agent can contain any IL-17-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains; (ii) a F(ab')$_2$ fragment, which is a bivalent fragment comprising two Fab fragments linked by a disulfide bridge at the hinge region; and (iii) a Fv fragment consisting of the $V_L$ and $V_H$ domains of a single arm of an antibody.

In one embodiment of the invention, the isolated IL-17-binding agent is an antibody or antibody fragment comprising (a) an immunoglobulin heavy chain polypeptide comprising the amino acid sequence of any one of SEQ ID NOs: 2-22, or SEQ ID NOs: 31-79, or a fragment thereof, and (b) an immunoglobulin light chain polypeptide comprising the amino acid sequence of SEQ ID NO: 24, SEQ ID NO: 25, SEQ ID NO: 26, SEQ ID NO: 27, SEQ ID NO: 28, SEQ ID NO: 80, or SEQ ID NO: 81, or a fragment thereof. In embodiments where the isolated IL-17-binding agent comprises a fragment of the immunoglobulin heavy chain or light chain polypeptide, the fragment can be of any size so long as the fragment binds to, and preferably inhibits the activity of, IL-17. In this respect, a fragment of the immunoglobulin heavy chain polypeptide desirably comprises between about 5 and 18 amino acids (e.g., about 5, 6, 7, 8, 9, 10, 11, 12, 13, 14, 15, 16, 17, 18, or a range defined by any two of the foregoing values). Similarly, a fragment of the immunoglobulin light chain polypeptide desirably comprises between about 5 and 18 amino acids (e.g., about 5, 6, 7, 8, 9, 10, 11, 12, 13, 14, 15, 16, 17, 18, or a range defined by any two of the foregoing values). When the IL-17-binding agent is an antibody or antibody fragment, the antibody or antibody fragment comprises a constant region ($F_c$) of any suitable class. Preferably, the antibody or antibody fragment comprises a constant region that is based upon wild type IgG1, IgG2, or IgG4 antibodies, or variants thereof.

The IL-17-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., *Science*, 242: 423-426 (1988); Huston et al., *Proc. Natl. Acad. Sci. USA*, 85: 5879-5883 (1988); and Osbourn et al., *Nat. Biotechnol.*, 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The isolated IL-17-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological subcellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated IL-17-binding agent can be, or can be obtained from, a human antibody, a non-human antibody, or a chimeric antibody. By "chimeric" is meant an antibody or fragment thereof comprising both human and non-human regions. Non-human antibodies include antibodies isolated from any non-human animal, such as, for example, a rodent (e.g., a mouse or rat). The immunoglobulin heavy chain polypeptide of the IL-17-binding agent can be obtained from a human antibody, a non-human antibody, or a chimeric antibody, independent of whether the immunoglobulin light chain polypeptide of the IL-17-binding agent is obtained from a human antibody, a non-human antibody, or a chimeric antibody. In other words, for example, the immunoglobulin heavy chain polypeptide can be obtained from a human antibody, and the immunoglobulin light chain polypeptide can be obtained from a non-human antibody. Conversely, the immunoglobulin heavy chain polypeptide can be obtained from a non-human antibody, and the immunoglobulin light chain polypeptide can be obtained from a human antibody. Alternatively, the immunoglobulin heavy chain polypeptide can be obtained from a rodent antibody or fragment thereof, and the immunoglobulin light chain polypeptide can be obtained from a human antibody or fragment thereof. This scenario may be useful, e.g., for the humanization of an antibody. In another embodiment, the immunoglobulin heavy chain polypeptide and the immunoglobulin light chain polypeptide are both obtained from a human antibody or a non-human antibody. Alternatively, the immunoglobulin heavy chain polypeptide and the immunoglobulin light chain polypeptide are both chimeric antibodies.

A human antibody, a non-human antibody, or a chimeric antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and C. A. Janeway et al. (eds.), *Immunobiology*, 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the HUMAB-MOUSE™, the Kirin TC MOUSE™, and the KM-MOUSE™ (see, e.g., Lonberg, *Nat. Biotechnol.*, 23(9): 1117-25 (2005), and Lonberg, *Handb. Exp. Pharmacol.*, 181: 69-97 (2008)).

In another embodiment of the invention, the isolated IL-17-binding agent can be part of an "alternative scaffold" or a fragment thereof. By "alternative scaffold" is meant a non-antibody polypeptide or polypeptide domain which displays an affinity and specificity towards an antigen of interest similar to that of an antibody. Exemplary alternative scaffolds include a β-sandwich domain such as from fibronectin (e.g., Adnectins), lipocalins (e.g., Anticalin), a Kunitz domain, thioredoxin (e.g., peptide aptamer), protein A (e.g., AFFIBODY™ molecules), an ankyrin repeat (e.g., DARPins), γ-β-crystallin or ubiquitin (e.g., AFFLIN™ molecules), CTLD3

(e.g., Tetranectin), and multivalent complexes (e.g., ATRI-MER™ molecules or SIMP™ molecules). Alternative scaffolds are described in, for example, Binz et al., *Nat. Biotechnol.*, 23: 1257-1268 (2005); Skerra, *Curr. Opin. Biotech.*, 18: 295-304 (2007); and U.S. Patent Application Publication 2009/0181855 A1.

In one embodiment, the alternative scaffold can be an AVIMER™ molecule. An AVIMER™ molecule is a class of therapeutic proteins from human origin unrelated to antibodies and antibody fragments, which are composed of several modular and reusable binding domains, referred to as A-domains (also referred to as class A module, complement type repeat, or LDL-receptor class A domain). AVIMER™ molecules were developed from human extracellular receptor domains by in vitro exon shuffling and phage display (Silverman et al., *Nat. Biotechnol.*, 23: 1493-94 (2005), and Silverman et al., *Nat. Biotechnol.*, 24: 220 (2006)). AVIMER™ molecules may comprise multiple independent binding domains that may exhibit improved affinity (in some cases sub-nanomolar) and specificity compared with single-epitope binding proteins (see, e.g., U.S. Patent Application Publications 2005/0221384 A1; 2005/0164301 A1; 2005/0053973 A1; 2005/0089932 A1; 2005/0048512 A1; and 2004/0175756 A1). Each of the known 217 human A-domains comprises about 35 amino acids (about 4 kDa). Native A-domains fold quickly and efficiently to a uniform, stable structure mediated primarily by calcium binding and disulfide formation. A conserved scaffold motif of only twelve amino acids is required for this common structure. An AVIMER™ molecule comprises multiple A-domains which are separated from one another by linkers that average five amino acids in length. The end result is a single protein chain containing multiple domains, each of which represents a separate function. Each domain of an AVIMER™ molecule binds an antigen independently, and the energetic contributions of each domain are additive.

The isolated IL-17-binding agent of the invention can be inserted into other molecules (e.g., polypeptides) to generate novel molecules which bind an antigen of interest. In this regard, the invention comprises a method of producing a polypeptide which binds IL-17, which comprises inserting the IL-17-binding agent into a different polypeptide. Such novel antigen-binding molecules can be generated using routine molecular biology techniques known in the art. For example, the IL-17-binding agent, or a nucleic acid sequence encoding the IL-17-binding agent can be inserted into a different molecule (e.g., a polypeptide or a polynucleotide) to generate a recombinant molecule that binds to IL-17. In one embodiment, a CDR (e.g., CDR1, CDR2, or CDR3) or a variable region of the immunoglobulin heavy chain polypeptide and/or the immunoglobulin light chain polypeptide described herein can be transplanted (i.e., grafted) into another molecule, such as an antibody or non-antibody polypeptide, using either protein chemistry or recombinant DNA technology. In this regard, the invention provides an isolated IL-17-binding agent comprising at least one CDR of an immunoglobulin heavy chain and/or light chain polypeptide as described herein. The isolated IL-17-binding agent can comprise one, two, or three CDRs of an immunoglobulin heavy chain and/or light chain variable region as described herein. In this regard, the CDR1 of the immunoglobulin heavy chain polypeptides described herein is located between amino acid residues 25 and 35, inclusive, of SEQ ID NOs: 2-22 and SEQ ID NOs: 31-79. The CDR2 of the immunoglobulin heavy chain polypeptides described herein is located between amino acid residues 50-67, inclusive, of SEQ ID NOs: 2-22 SEQ ID NOs: 31-79. The CDR3 of the immunoglobulin heavy chain polypeptides described herein is located between amino acid residues 99 and 102, inclusive, of SEQ ID NOs: 2-22 and SEQ ID NOs: 31-79. The locations of the CDRs of each of the immunoglobulin light chain polypeptides described herein are set forth in Table 1.

TABLE 1

| SEQ ID NO | Location of CDR1 (residues of SEQ ID NO) | Location of CDR2 (residues of SEQ ID NO) | Location of CDR3 (residues of SEQ ID NO) |
|---|---|---|---|
| 24 | 24-35 (inclusive) | 51-57 (inclusive) | 90-98 (inclusive) |
| 25 | 24-35 (inclusive) | 51-57 (inclusive) | 90-98 (inclusive) |
| 26 | 24-34 (inclusive) | 50-56 (inclusive) | 89-97 (inclusive) |
| 27 | 24-40 (inclusive) | 56-62 (inclusive) | 95-104 (inclusive) |
| 28 | 24-35 (inclusive) | 51-57 (inclusive) | 90-98 (inclusive) |

In another embodiment, the entire variable region of the immunoglobulin heavy chain polypeptide and/or the immunoglobulin light chain polypeptide described herein can be transplanted in place of the variable region of a LC and/or a HC of another antibody.

The aforementioned methods and molecules may be useful, for example, to generate an antibody comprising an Fc region of a different isotype or an Fc region that is conjugated to a protein or non-protein moiety (e.g., a fluorescent tag or a chemotherapeutic agent). The invention also provides a conjugate of (1) an antibody, an alternative scaffold, or fragments thereof, and (2) a protein or non-protein moiety comprising the IL-17-binding agent. For example, the IL-17-binding agent can be part of an antibody conjugated to a peptide, a fluorescent molecule, or a chemotherapeutic agent.

The invention further provides a vector comprising a nucleic acid sequence encoding the isolated IL-17-binding agent (e.g., the immunoglobulin heavy chain polypeptide and/or the immunoglobulin light chain polypeptide described herein). A "nucleic acid" is intended to encompass a polymer of DNA or RNA, i.e., a polynucleotide, which can be single-stranded or double-stranded and which can contain non-natural or altered nucleotides. Nucleic acids are typically linked via phosphate bonds to form nucleic acids or polynucleotides, though many other linkages are known in the art (e.g., phosphorothioates, boranophosphates, and the like).

The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid encoding the IL-17-binding agent, the vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), *Fundamental Immunology*, 3rd Edition, Raven Press, New York (1993), pages 353-363; and U.S. Pat. No. 5,885,827).

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 92/08796 and WO 94/28143; Wigler et al., *Proc. Natl. Acad. Sci. USA*, 77: 3567 (1980); O'Hare et al., *Proc. Natl. Acad. Sci. USA*, 78: 1527 (1981); Mulligan & Berg, *Proc. Natl. Acad. Sci. USA*, 78: 2072 (1981); Colberre-Garapin et al., *J. Mol. Biol.*, 150:1 (1981); Santerre et al., *Gene*, 30: 147 (1984); Kent et al., *Science*, 237: 901-903 (1987); Wigler et al., *Cell*, 11: 223 (1977); Szybalska & Szybalski, *Proc. Natl. Acad. Sci. USA*, 48: 2026 (1962); Lowy et al., *Cell*, 22:817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy* 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.), and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

The nucleic acid sequence encoding the immunoglobulin heavy chain polypeptide and the nucleic acid sequence encoding the immunoglobulin light chain polypeptide of the IL-17-binding agent can be provided to a cell on the same vector (i.e., in cis). A bidirectional promoter can be used to control expression of both nucleic acid sequences. In another embodiment, a unidirectional promoter can control expression of both nucleic acid sequences. The nucleic acid sequence encoding the immunoglobulin heavy chain polypeptide and the nucleic acid sequence encoding the immunoglobulin light chain polypeptide alternatively can be provided to the population of cells on separate vectors (i.e., in trans). The vector comprising the nucleic acid sequence encoding the immunoglobulin heavy chain polypeptide can comprise the same or different expression control sequences as the vector comprising the nucleic acid sequence encoding the immunoglobulin light chain polypeptide. The separate vectors can be provided to cells simultaneously or sequentially.

The vector(s) comprising the nucleic acid(s) encoding the IL-17-binding agent can be introduced into a host cell that is capable of expressing the polypeptides encoded thereby, including any suitable prokaryotic or eukaryotic cell. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vectors are introduced into a eukaryotic cell. Suitable eukaryotic cells are known in the art and include, for example, yeast cells, insect cells, and mammalian cells. Examples of suitable yeast cells include those from the genera *Hansenula*, *Kluyveromyces*, *Pichia*, *Rhino-spo-*

*ridium, Saccharomyces,* and *Schizosaccharomyces.* Preferred yeast cells include, for example, *Saccharomyces cerivisae* and *Pichia pastoris.*

Suitable insect cells are described in, for example, Kitts et al., *Biotechniques,* 14: 810-817 (1993); Lucklow, *Curr. Opin. Biotechnol.,* 4: 564-572 (1993); and Lucklow et al., *J. Virol.,* 67: 4566-4579 (1993). Preferred insect cells include Sf-9 and HI5 (Invitrogen, Carlsbad, Calif.).

Preferably, mammalian cells are utilized in the invention. A number of suitable mammalian host cells are known in the art and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA,* 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

A nucleic acid sequence encoding the IL-17-binding agent may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols,* Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell. Biol.,* 7: 2031-2034 (1987)). Phage or viral vectors can be introduced into host cells, after growth of infectious particles in suitable packaging cells many of which are commercially available.

The invention provides a composition comprising the isolated IL-17-binding agent or the vector encoding the IL-17 binding agent described herein. Preferably, the composition is a pharmaceutically acceptable (e.g., physiologically acceptable) composition, which comprises a carrier, preferably a pharmaceutically (e.g., physiologically acceptable) carrier, and the IL-17-binding agent. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy,* 21$^{st}$ *Edition,* Lippincott Williams & Wilkins, Philadelphia, Pa. (2001).

The invention further provides a method of treating an IL-17-mediated disease in a mammal. The method comprises administering the aforementioned composition to a mammal having an IL-17-mediated disease, whereupon the IL-17-mediated disease is treated in the mammal. The term "IL-17-mediated disease," as used herein, refers to any disease or disorder in which the presence of IL-17 causes or contributes to the pathological effects of the disease, or a decrease in IL-17 levels or activity has a therapeutic benefit in mammals, preferably humans. Examples of IL-17-mediated diseases include, but are not limited to, airway inflammation, asthma, rheumatoid arthritis (RA), osteoarthritis, osteoporosis, bone erosion, intraperitoneal abscesses and adhesions, inflammatory bowel disorder (IBD), chronic obstructive pulmonary disorder (COPD), Addison's disease, agammaglobulinemia, allergic asthma, alopecia greata, Celiac spruce, Chagas disease, idiopathic pulmonary fibrosis, Crohn's disease, ulcerative colitis, allograft rejection (e.g., renal), psoriatic arthritis, uveitis, Behcet's disease, certain types of cancer, angiogenesis, atherosclerosis, multiple sclerosis (MS), systemic lupus erythematosus, septicemia, septic or endotoxic shock, response to allergen exposure, *Helicobacter pylori*-associated gastritis, bronchial asthma, ankylosing spondylitis, lupus nephritis, psoriasis, ischemia, systemic sclerosis, stroke, and other inflammatory disorders.

As used herein, the terms "treatment," "treating," and the like, refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the IL-17-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the IL-17-binding agent to elicit a desired response in the individual. For example, a therapeutically effective amount of an IL-17-binding agent of the invention is an amount which decreases IL-17 bioactivity in a human (e.g., by blocking binding to IL17R).

Alternatively, the pharmacologic and/or physiologic effect may be prophylactic, i.e., the effect completely or partially prevents a disease or symptom thereof. In this respect, the inventive method comprises administering a "prophylactically effective amount" of the IL-17-binding agent to a mammal that is predisposed to an IL-17-mediated disease. A "prophylactically effective amount" refers to an amount effective, at dosages and for periods of time necessary, to achieve a desired prophylactic result (e.g., prevention of disease onset).

A typical dose can be, for example, in the range of 0.001 to 1000 µg; however, doses below or above this exemplary range are within the scope of the invention. The daily parenteral dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values). Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising the IL-17-binding agent of the invention can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive IL-17-binding agent can be measured by any suitable method known in the art. For example, the biological activity can be assessed by determining the stability of a particular IL-17-binding agent. In one embodiment of the invention, the IL-17-binding agent (e.g., an antibody) has an in vivo half life between about 5 and 28 days (e.g., about 5, 6, 7, 8, 9, 10, 11, 12, 13, 14, 15, 16, 17, 18, 19, 20, 21, 22, 23, 24, 25, 26, 27, 28, or a range defined by any two of the foregoing values). Preferably, the IL-17-binding agent has an in vivo half life between about 21 days and 28 days (e.g., 21, 22, 23, 24, 25, 26, 27, or 28 days). The biological activity of a particular IL-17-binding agent also can be assessed by determining its binding affinity to IL-17 or an epitope thereof. The term "affinity" refers to the equilibrium constant for the reversible binding of two agents and is expressed as the dissociation constant (KD). Affinity of a binding agent to a ligand, such as affinity of an antibody for an epitope, can be, for example, from about 100 nanomolar (nM) to about 0.1 nM, from about 100 nM to about 1 picomolar (pM), from about 1 nM to about 1 pM, or from about 1 nM to about 1 femtomolar (fM). In the context of the inventive method, the IL-17-binding agent binds to IL-17 with a KD less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values), and preferably less than or equal to 200 picomolar (e.g., 190 pmol, 175 pmol, 150 pmol, 125 pmol, 110 pmol, 100 pmol, 90 pmol, 80 pmol, 75 pmol, 60 pmol, 50 pmol, 40 pmol, 30 pmol, 25 pmol, 20 pmol, 15 pmol, 10 pmol, 5 pmol, 1 pmol, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), antigen panning, and/or ELISA (see, e.g., Janeway et al. (eds.), *Immunobiology*, 5$^{th}$ ed., Garland Publishing, New York, N.Y., 2001).

The IL-17-binding agent of the invention may be administered alone or in combination with other drugs (e.g., as an adjuvant). For example, the IL-17 binding agent can be administered in combination with immunosuppressive or immunomodulating agents or other anti-inflammatory agents for the treatment or prevention of the IL-17-mediated diseases disclosed herein. In this respect, the IL-17-binding agent can be used in combination with disease-modifying anti-rheumatic drugs (DMARD) (e.g., gold salts, sulphasalazine, antimalarias, methotrexate, D-penicillamine, azathioprine, mycophenolic acid, cyclosporine A, tacrolimus, sirolimus, minocycline, leflunomide, and glucocorticoids), a calcineurin inhibitor (e.g., cyclosporin A or FK 506), a modulator of lymphocyte recirculation (e.g., FTY720 and FTY720 analogs), an mTOR inhibitor (e.g., rapamycin, 40-O-(2-hydroxyethyl)-rapamycin, CCI779, ABT578, AP23573, or TAFA-93), an ascomycin having immuno-suppressive properties (e.g., ABT-281, ASM981, etc.), corticosteroids, cyclophosphamide, azathioprene, methotrexate, leflunomide, mizoribine, mycophenolic acid, mycophenolate mofetil, 15-deoxyspergualine, or an immunosuppressive homologue, analogue or derivative thereof, immunosuppressive monoclonal antibodies (e.g., monoclonal antibodies to leukocyte receptors such as MHC, CD2, CD3, CD4, CD7, CD8, CD25, CD28, CD40. CD45, CD58, CD80, CD86, or their ligands), other immunomodulatory compounds, adhesion molecule inhibitors (e.g., LFA-1 antagonists, ICAM-1 or -3 antagonists, VCAM-4 antagonists, or VLA-4 antagonists), a chemotherapeutic agent (e.g., paclitaxel, gemcitabine, cisplatinum, doxorubicin, or 5-fluorouracil), anti-TNF agents (e.g. monoclonal antibodies to TNF such as infliximab, adalimumab, CDP870, or receptor constructs to TNF-RI or TNF-RII, such as ENBREL™ (Etanercept) or PEG-TNF-RI), blockers of proinflammatory cytokines, IL-1 blockers (e.g., KINERET™ (Anakinra) or IL-1 trap, AAL160, ACZ 885, and IL-6 blockers), chemokine blockers (e.g., inhibitors or activators of proteases), anti-IL-15 antibodies, anti-IL-6 antibodies, anti-CD20 antibodies, NSAIDs, and/or an anti-infectious agent.

In addition to therapeutic uses, the IL-17-binding agent described herein can be used in diagnostic or research applications. In this respect, the IL-17-binding agent can be used in a method to diagnose an IL-17-mediated disease or disorder. For example, the invention provide a method of diagnosing an IL-17-mediated disease in a mammal which comprises administering the IL-17-binding agent to a mammal suspected of having an IL-17-mediated disease, whereupon detection of the IL-17-binding agent binding to IL-17 is indicative of the mammal having an IL-17-mediated disease. In a similar manner, the IL-17-binding agent can be used in an assay to monitor IL-17 levels in a subject being tested for an IL-17-associated disease or disorder. Research applications include, for example, methods that utilize the IL-17-binding agent and a label to detect IL-17 in a sample, e.g., in a human body fluid or in a cell or tissue extract. The IL-17-binding agent can be used with or without modification, such as covalent or non-covalent labeling with a detectable moiety. For example, the detectable moiety can be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin), or an enzyme (e.g., alkaline phosphatase, beta-galactosidase, or horseradish peroxidase). Any method known in the art for separately conjugating an antigen-binding agent (e.g., an antibody) to a detectable moiety may be employed in the context of the invention (see, e.g., Hunter et al., *Nature,* 144: 945 (1962); David et al., *Biochemistry,* 13: 1014 (1974); Pain et al., *J. Immunol. Meth.,* 40: 219 (1981); and Nygren, *J. Histochem. and Cytochem.,* 30: 407 (1982)).

IL-17 levels can be measured using the inventive IL-17-binding agent by any suitable method known in the art. Such methods include, for example, ELISA, radioimmunoassay (RIA), and FACS. Normal or standard expression values of IL-17 can be established using any suitable technique, e.g., by combining a sample comprising, or suspected of comprising, an IL-17 polypeptide with an IL-17-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of IL-17 polypeptide expressed in a sample is then compared with the standard values.

The IL-17-binding agent can be provided in a kit, i.e., a packaged combination of reagents in predetermined amounts with instructions for performing a diagnostic assay. If the IL-17-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

Example 1

This example demonstrates that an IL-17-binding agent in accordance with the invention can block the activity of human IL-17 in vivo.

Human IL-17 (hIL-17) is able to bind and stimulate the mouse IL-17 receptor leading to the subsequent release of KC(CXCL1) chemokine Time and dose ranging experiments were performed to identify the optimal dose of hIL-17 that resulted in the maximum induction of mouse KC in vivo. Human IL-17 was administered subcutaneously to mice at 1, 3, and 10 µg/mouse. At various time-points after hIL-17 administration (FIG. 1), mice were sacrificed and KC levels were determined by ELISA using a commercially available kit according to the manufacturer's instructions (KC Quantikine, R&D Systems, Minneapolis, Minn.). These experiments indicated that a subcutaneous dose of 10 µg/mouse of human IL-17 resulted in the maximum levels of KC in mouse serum two hours post administration of the human cytokine (FIG. 1).

Figure 2:
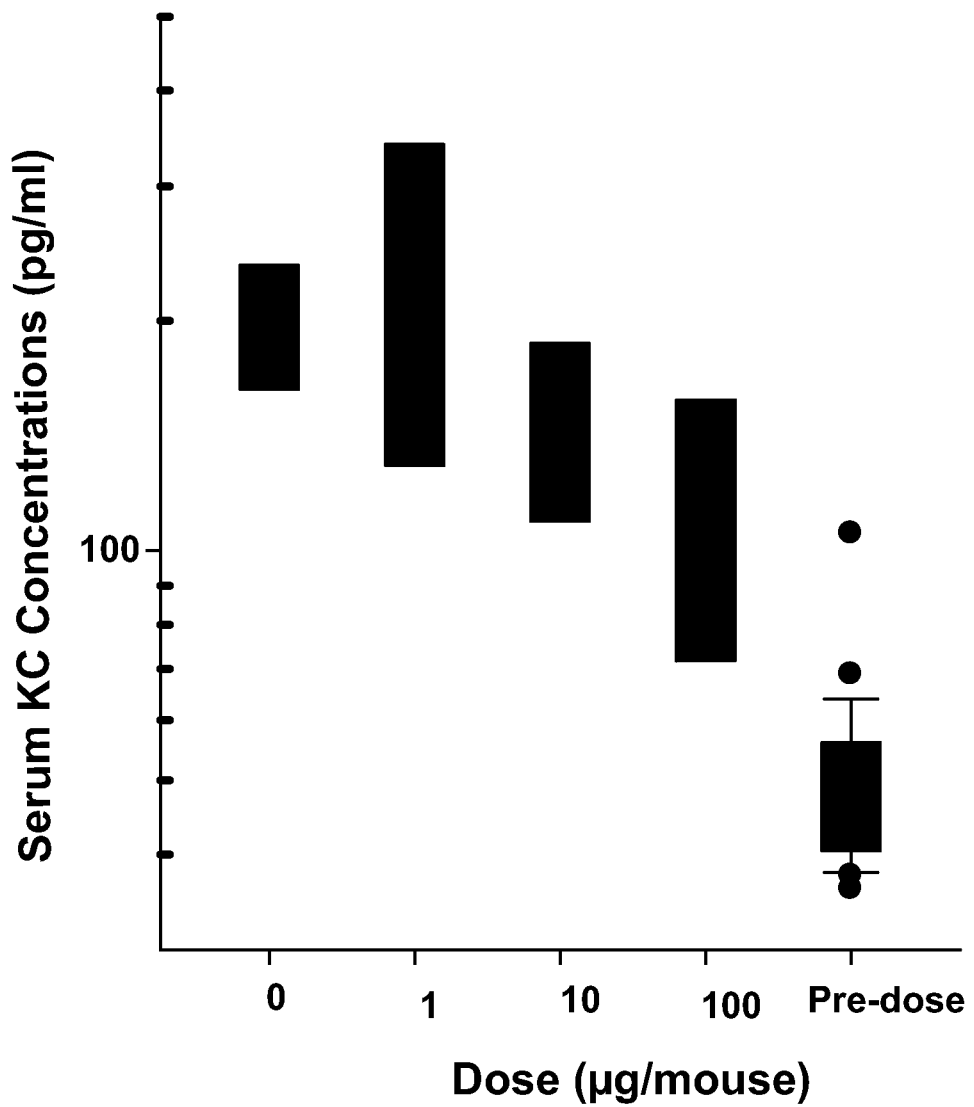
FIG. 2 is a graph illustrating dose-dependent suppression of serum KC levels two-hours following administration of hIL-17 in mice by an anti-IL17 antibody (SEQ ID NO: 4 paired with SEQ ID NO: 24).

A full length IgG1 antibody comprising a heavy chain polypeptide comprising SEQ ID NO: 4 and a light chain polypeptide comprising SEQ ID NO: 24 was administered intravenously to mice at 1, 10, and 100 µg/mouse two hours prior to subcutaneous injection of hIL-17. Two hours after human IL-17 administration, mice were sacrificed and KC levels were determined by ELISA using a commercially available kit. An isotype-matched (IgG1) antibody was used as negative control (NC). As shown in FIG. 2, the antibody comprising SEQ ID NO: 4 and SEQ ID NO: 24 blocks the ability of hIL-17 to stimulate the mouse IL-17 receptor dose-dependently. At the dose of 100 µg/mouse, the antibody decreased mean KC levels by approximately 75 to 80% compared to the vehicle and NC antibody, which had no effect.

The result of this example demonstrate that an IL-17 specific antibody comprising SEQ ID NO: 4 and SEQ ID NO: 24 can inhibit the activity of IL-17 in vivo.

Example 2

This example demonstrates that immunoglobulin heavy chain (HC) and light chain (LC) polypeptides described herein can form antibodies that bind IL-17 in vitro.

DNA samples encoding various immunoglobulin heavy chain (HC) and light chain (LC) polypeptides as described herein were prepared by combining the following: 20'11 maxi-prepped DNA (comprised of 0.2 µg HC and 0.2 µg LC plasmid), 9.8 µg OPTIMEM™ (Invitrogen, Carlsbad, Calif.), 1.2 µl GENEJUICE™ Transfection Reagent (Novagen, Gibbstown, N.J.), and 13.8 µl OPTIMEM™ (pre-warmed). Following thorough mixing and incubation (at room temperature) of the DNA preparations, 35 µl of reagent/DNA mix was added to 5×10⁴ HEK293-c18 cells. 18 hours prior to transfection, the cells were plated in 150 ill of Freestyle media per well of a 96-well microtiter dish and incubated at 37° C. in 8% $CO_2$ humidified atmosphere. Following transfection, cells were returned to 37° C. in 8% $CO_2$. The combinations of heavy chain and light chain sequences that were tested are set forth in Table 2.

TABLE 2

| Well # | Heavy Chain SEQ ID NO: | Light Chain SEQ ID NO: |
|---|---|---|
| 1 | 30 | 29 |
| 2 | 1 | 29 |
| 3 | 2 | 29 |
| 4 | 4 | 29 |
| 5 | 6 | 29 |
| 6 | 7 | 29 |
| 7 | 9 | 29 |
| 8 | 30 | 24 |
| 9 | 1 | 24 |
| 10 | 2 | 24 |
| 11 | 4 | 24 |
| 12 | 6 | 24 |
| 13 | 7 | 24 |
| 14 | 9 | 24 |
| 15 | 30 | 25 |
| 16 | 4 | 25 |
| 17 | 6 | 25 |
| 18 | 30 | 27 |
| 19 | 4 | 27 |
| 20 | 6 | 27 |

Figure 3:
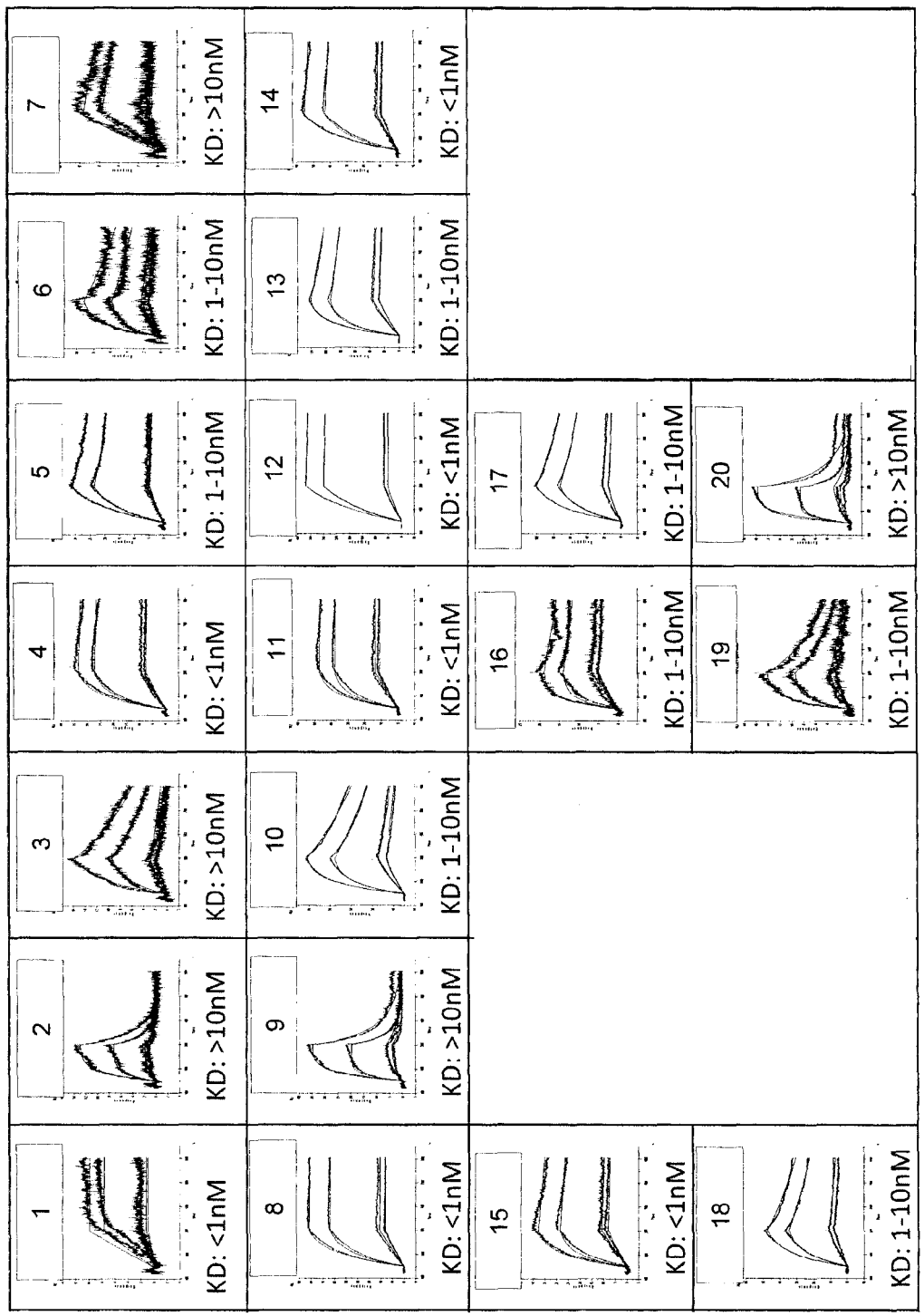
FIG. 3 is a diagram which illustrates BIACORE™ A100 dissociation curves for HC and LC combinations described in Example 2.

Supernatants in 96-well plates were harvested 5-7 days post transfection. Prior to loading onto BIACORE™ A100 and/or BIACORE™ 4000 (GE Healthcare, Buckinghamshire, United Kingdom), plates were spun down at 1500 rpm for 5 minutes to remove air bubbles. Positive, negative, and media controls were spiked into empty wells. An anti-human Fc specific IgG was amine-coupled to the Sensor Chip CM5 surface at two different densities on two spots of a given flowcell for 2 over 2 analyses. The IgGs of interest were captured at both densities. Two concentrations of antigen (human IL-17) were flowed over each antibody at each density (including a "zero concentration" sampling) and monitored for binding interactions. Surface was regenerated with 10 mM glycine at pH 1.7 to remove material that was bound to the capture antibody. The data set was analyzed with 1:1 interaction Langelier mode with mass transport. The tested heavy chain and light chain polypeptides formed antibodies that bind to human IL-17 (see FIG. 3).

The results of this example demonstrate that an IL-17-binding agent comprising the immunoglobulin heavy and light chain polypeptides described herein can bind to human IL-17 in vitro.

Example 3

This example demonstrates that immunoglobulin heavy chain (HC) and light chain (LC) polypeptides described herein can form antibodies that bind to human IL-17 in vitro.

The rank order of binding affinity for the following anti-IL17a antibodies was determined by a homogeneous time resolved fluorescence (HTRF) assay: (a) an antibody comprising a heavy chain polypeptide comprising SEQ ID NO: 55 and a light chain polypeptide comprising SEQ ID NO: 24 ("APE508"), (b) an antibody comprising a heavy chain polypeptide comprising SEQ ID NO: 78 and a light chain polypeptide comprising SEQ ID NO: 24 ("APE755"), (c) a first reference anti-IL17a antibody (described in International Patent Application Publication No. WO 2006/013107), and (d) a second reference anti-IL17a antibody (described in U.S. Pat. No. 7,838,738). In the assay, an IL-17 antigen (APE349-SEQ ID NO: 82) linked to wasabi fluorescent protein (WFP) (see, e.g., Ai et al., *BMC Biol.*, 6:13 (2008)) was labeled with N-hydroxysuccinimide activated cryptate (Eu3+-TBP-NHS Cryptate) using an HTRF® Cryptate Labeling Kit following manufacturer's protocol (Cisbio US, Bedford, Mass.). A biotinylated version of the second reference antibody was linked to Streptavidin-XL665 (Cisbio US, Bedford, Mass.) and subsequently mixed with each of the aforementioned anti-IL17a antibodies at various concentrations. The antibodies were then incubated with the labeled antigen overnight at room temperature. At the end of the assay, the reaction was read in a ProxiPlate-384 Plus (Perkin Elmer, Waltham, Mass.) using an EnVision Multilabel Plate Reader (PerkinElmer, Waltham, Mass.). The binding of the labeled antigen and the reference antibody was determined as the ratio of 665 nm to 620 nm. The ratios were plotted against the concentrations of the tested antibodies, and the $IC_{50}$ for each tested antibody was determined by inhibitory curve fitting using GraphPad Prism software (GraphPad Software, Inc., La Jolla, Calif.). The results of this assay demonstrate that the APE755 and APE508 antibodies bind to the same epitope on IL-17 as the reference anti-IL17a antibodies.

A cytokine release assay using HT1080 cells, NIH 3T3 cells, or primary synovial fibroblast cells from rheumatoid arthritis patients (RA SFB) cells also was used to demonstrate that immunoglobulin heavy chain (HC) and light chain (LC) polypeptides described herein can form antibodies that bind to human IL-17. IL-6 release from NIH3T3 and HT-1080 cells was quantified by ELISA. Cells were seeded in a 96-well assay plate at $1 \times 10^4$ cells/well and were then treated for 24 hours with (i) purified human Myc-IL-17a (APE280, 52 pM for NIH3T3 cells or 200 pM for HT1080 cells), (ii) human recombinant TNFα (R&D Systems, Inc., Minneapolis, Minn., 0.5 ng/mL; NIH3T3 cells only), and (iii) the anti-IL17a antibodies described above at various concentrations (all in 100'11 DMEM/10% FCS). After treatment, 10'11 supernatant from each well was analyzed by ELISA (eBioscience, Inc., San Diego, Calif.) for mouse IL-6 quantification following the manufacturer's protocol. The IL-6 levels were normalized to the negative control, in which no anti-IL17a antibody was present during the treatment. The normalized IL-6 levels were plotted versus antibody concentration, and the $IC_{50}$ for each antibody was determined by inhibitory curve fitting using GraphPad Prism software. IL-17a-stimulated IL-8 release from HT-1080 cells was measured as described above except that 800 pM Myc-IL-17a and 0.05 ng/mL of human recombinant TNFα was used. Quantification of IL-8 was performed using a BioLegend ELISA kit (San Diego, Calif.) following the manufacturer's protocol.

The APE755 antibody inhibited IL-6 release from human IL-17-stimulated cell lines with 5-10 fold higher potency than the first reference anti-IL17a antibody. The APE755 antibody inhibited IL-8 release from human IL-17-stimulated cell lines with 2-fold higher potency than the first reference anti-IL17a antibody.

IL-6 and IL-8 release from RA SFB cells was quantified by ELISA. RA SFB cells at passage 2-4 (Asterand, Mich., isolated from diseased region of the knee from a 63 year-old Caucasian female with rheumatoid arthritis) were seeded in a 96-well assay plate at $5 \times 10^3$ cells/well. After overnight culture, the cells were treated for 24 hours with human IL-17a (Humanzyme, IL, 200 pM) and various concentrations of one of the following anti-IL17a antibodies: (a) APE508, (b) APE755, (c) a first reference anti-IL17a antibody (described in International Patent Application Publication No. WO 2006/013107), (d) a second reference anti-IL17a antibody (described in U.S. Pat. No. 7,838,738), and (e) an antibody specific for nerve growth factor (NGF) ("APE409"), which served as a negative control (all in 100 µl DMEM/F-12/10% FBS). After treatment, 10 µl or 20 µl of supernatant from each well was subjected to human IL-6 (eBioscience, Inc., San Diego, Calif.) or human IL-8 (BioLegend, San Diego, Calif.) ELISA, respectively, following the manufacturers' protocols. The IL-6 and IL-8 levels were normalized to the negative controls (i.e., no anti-IL-17a antibody present during treatment). The normalized levels were plotted as described above.

Figure 4:
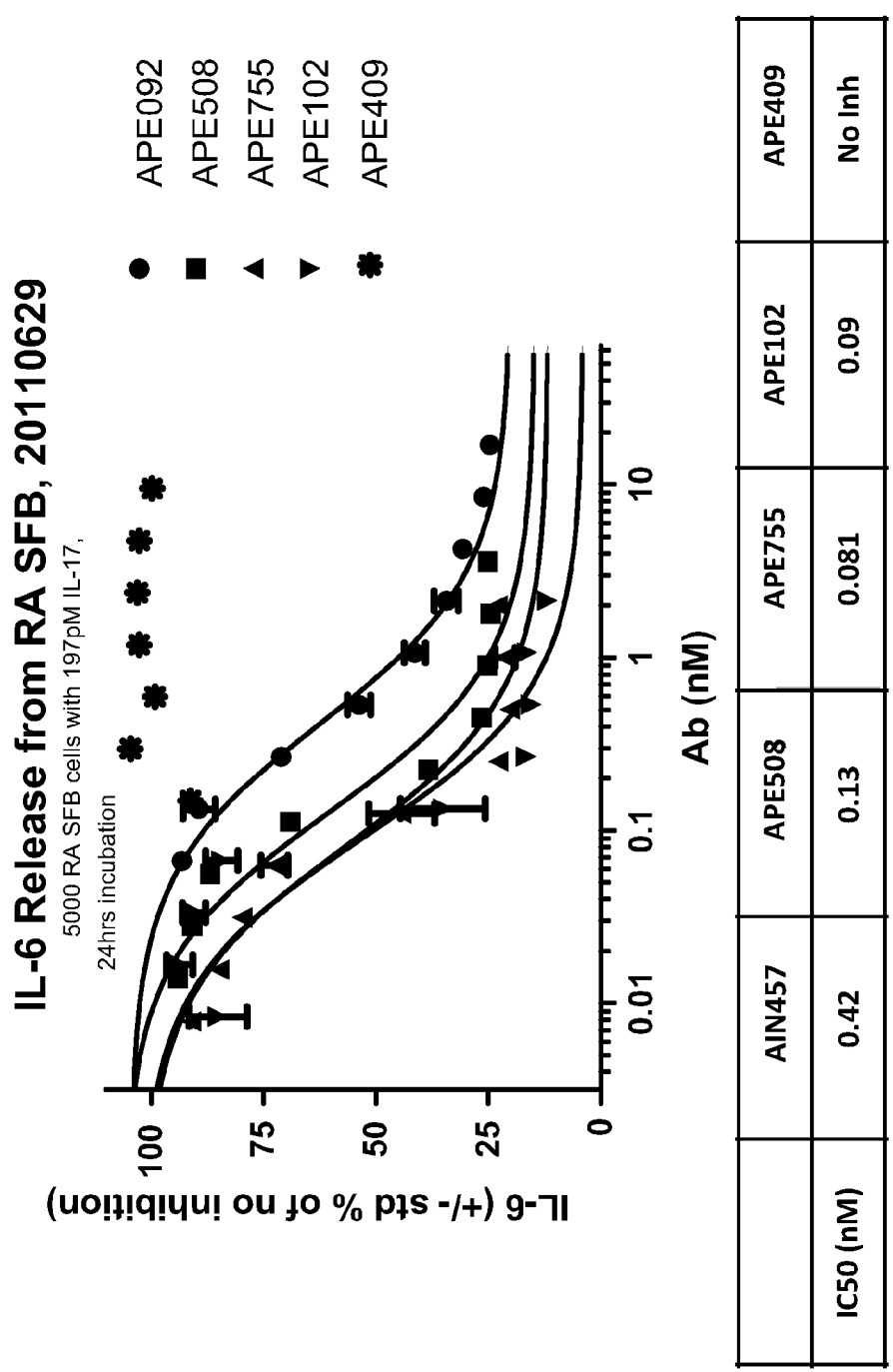
FIG. 4 is a graph illustrating the results of an IL-6 release assay in human RA synovial fibroblasts described in Example 3.

The APE755 antibody inhibited IL-6 and IL-8 release from IL-17-stimulated primary human RA synovial fibroblasts with a 5-fold higher potency than the reference anti-IL-17a antibodies (see FIG. 4).

The results of this example demonstrate that an IL-17-binding agent comprising the immunoglobulin heavy and light chain polypeptides described herein can bind to human IL-17 in vitro.

Example 4

This example demonstrates that immunoglobulin heavy chain (HC) and light chain (LC) polypeptides described herein can form antibodies that block the activity of IL-17 in vitro.

Figure 5:
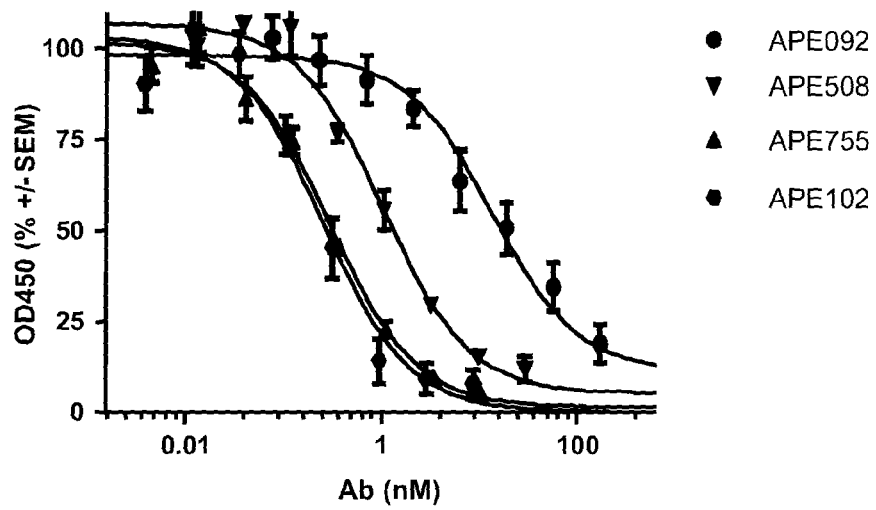
FIG. 5 is a graph illustrating the results of an ELISA assay that was used to measure inhibition of receptor-ligand binding by anti-IL17a antibodies described in Example 4.

The inhibition of receptor-ligand binding by anti-IL17a antibodies was quantified by competition ELISA. A 96-well assay plate was coated with 5 nM myc-IL-17a (APE280) in 100 µl coating buffer (eBioscience, Inc., Sand Diego, Calif.). 1 nM biotinylated IL-17 receptor A (IL-17RA) (R&D Systems, Inc., Minneapolis, Minn.) was mixed with various concentrations of the anti-IL17a antibodies described in Example 3 (all in 100 µl blocking buffer (eBioscience, Inc., San Diego, Calif.)), and incubated for 24 hours in the IL-17A coated plate. The captured biotinylated IL-17RA was quantified by using avidin-horseradish peroxidase (HRP) following a standard ELISA protocol. The signals were normalized to the negative control, in which no anti-IL17a antibody was present to block the binding. The normalized receptor-ligand binding signals were plotted against the concentrations of the antibodies, and the $IC_{50}$ for each antibody was determined by inhibitory curve fitting using GraphPad Prism software. The antibody APE755 was 40-fold more potent than the first reference anti-IL-17a antibody, and equivalent to the second anti-IL-17a reference antibody, in blocking IL-17/IL-17RA interaction (FIG. 5).

The results of this example demonstrate that an IL-17 specific antibody comprising a heavy chain polypeptide comprising SEQ ID NO: 78 and a light chain polypeptide comprising SEQ ID NO: 24 can inhibit the activity of IL-17 in vitro.

Example 5

This example demonstrates that immunoglobulin heavy chain (HC) and light chain (LC) polypeptides described herein can form antibodies that bind to human IL-17 in vitro.

The binding affinities of various antibodies comprising immunoglobulin heavy chain (HC) and light chain (LC) polypeptides described herein were evaluated using BIACORE™ and KINEXA® assays.

BIACORE T100™ is used to determine antibody-antigen binding kinetics and affinity. The technology is based on surface plasmon resonance (SPR), an optical phenomenon that enables detection of label-free interactions in real time within a dextran biosensor matrix. It is therefore suited for measuring rate constants of association ($k_{on}$) as well as dissociation ($k_{off}$). All reagents and materials were purchased from GE Healthcare (Buckinghamshire, United Kingdom). Anti-IL17a antibodies were captured by an anti-human Fc antibody (GE Healthcare; Catalog No. BR-1008-39) that was covalently immobilized onto a CM5 sensor chip (GE Healthcare; Catalog No. BR-1005-30) using amine coupling chemistry. 3000 response units (RU) of capture antibody were attached to the dextran surface, and 30-50 RU's of 500 ng/mL anti-IL-17a antibodies were subsequently captured. 1×HBS-EP+ buffer (of 0.01M HEPES, 0.15M NaCl, 3 mM EDTA, 0.05% Polysorbate, pH 7.6) was used to reconstitute antigen at various concentrations (starting at 50 nM and using two-fold serial dilutions for each concentration). 210 μL of each antigen concentration was injected over captured antibody at a flow rate of 30 μL/min, then allowed to dissociate for 10 minutes. Surface was regenerated with 60 μL of 3M $MgCl_2$ after each cycle to establish baseline. Association and dissociation kinetic constants ($k_a$ and $k_d$) were evaluated with "1:1 with mass transport" binding model in the BIACORE™ T100 Evaluation Software. The degree of binding for the BIACORE™ assay was measured as "++" (strong binding), "+" (binding), or "+/−" (close to background). The results of the BIACORE™ assay are set forth in Table 3.

TABLE 3

| Heavy Chain SEQ ID NO: | Light Chain SEQ ID NO: | Clone Name | BIACORE ™ 4000 +/− binding |
|---|---|---|---|
| 1 | 24 | 546/773 | + |
| 4 | 25 | 817/772 | + |
| 4 | 27 | 817/842 | + |
| 9 | 24 | 843/773 | + |
| 8 | 24 | 846/773 | + |
| 10 | 25 | 847/772 | + |
| 10 | 27 | 847/842 | + |
| 12 | 25 | 878/772 | + |
| 12 | 27 | 878/842 | + |
| 13 | 25 | 887/772 | + |
| 13 | 26 | 887/841 | + |
| 13 | 27 | 887/842 | + |

TABLE 3-continued

| Heavy Chain SEQ ID NO: | Light Chain SEQ ID NO: | Clone Name | BIACORE ™ 4000 +/− binding |
|---|---|---|---|
| 14 | 24 | 1102/773 | + |
| 21 | 24 | 1103/773 | + |
| 33 | 24 | 1129/773 | + |
| 34 | 24 | 1134/773 | + |
| 32 | 24 | 1137/773 | + |
| 35 | 24 | 1139/773 | + |
| 17 | 24 | 1142/773 | + |
| 77 | 24 | 1143/773 | + |
| 76 | 24 | 1144/773 | + |
| 19 | 24 | 1146/773 | + |
| 15 | 24 | 1147/773 | + |
| 36 | 24 | 1153/773 | + |
| 84 | 24 | MP4-2 | + |
| 85 | 24 | MP4-4 | ++ |
| 86 | 24 | MP4-5 | ++ |
| 87 | 24 | MP4-6 | + |
| 88 | 24 | MP4-7 | + |
| 89 | 24 | MP4-8 | + |
| 90 | 24 | MP4-9 | + |
| 91 | 24 | MP4-10 | + |
| 92 | 24 | MP4-11 | + |
| 93 | 24 | MP4-14 | + |
| 94 | 24 | MP4-16 | + |
| 95 | 24 | MP4-17 | + |
| 96 | 24 | MP4-19 | +/− |
| 97 | 24 | MP4-20 | + |
| 98 | 24 | MP4-21 | + |
| 99 | 24 | MP4-22 | + |
| 100 | 24 | MP4-23 | ++ |

Antibodies optimized to ≤100 pM also were characterized using a KINEXA® 3000 assay (Sapidyne Instruments, Boise, Id.). KINEXA® technology measures the unbound/free receptor molecule in solution phase. Measuring binding events in the solution phase with micro beads for maximized surface area avoids mass transport limitations and mobility effects inherent to methods that measure binding to a solid phase. For each experiment, 50 μg of human IL-17a was amine-coupled to 50 mg of UltraLink Biosupport beads (Thermo Scientific, Waltham, Mass.; Catalog No. 53110). A constant concentration of antibody (sufficient to produce 0.8 V-1.2 V of signal) was incubated for a sufficient period of time to approach or to reach equilibrium (time of incubation varies for each antibody and is dependent on affinity) with titrated antigen in sample buffer (1×PBS, pH 7.4, 0.02% $NaN_3$, 0.1% BSA). Antibody-antigen solution was then flown over antigen-coupled beads at a rate of 0.25 mL/min. Free antibody captured by beads was detected using Cy5-conjugated AffiniPure Donkey Anti-Human IgG (H+ L) (Jackson ImmunoResearch; Catalog No: 709-175-149). The $K_d$ and/or ABC (active binding concentration) of antibody was obtained from non-linear regression analysis using a one-site homogeneous binding model in the KINEXA® Pro Software. In order to achieve the most accurate measurement for each antibody, each "$K_d$ controlled curve" (wherein the antibody concentration is below the $K_d$) was combined with the "receptor controlled curve" (where antibody concentration is well above the $K_d$) in N-curve analysis. The results of the KINEXA® assay are set forth in Table 4.

TABLE 4

| Heavy Chain SEQ ID NO: | Light Chain SEQ ID NO: | Clone Name | Average KINEXA ® values | | |
|---|---|---|---|---|---|
| | | | $k_a$ (1/Ms) | $k_d$ (1/s) | KD |
| 2 | 24 | APE253-771/773 | not determined (ND) | ND | ~60 nM |

TABLE 4-continued

| Heavy Chain SEQ ID NO: | Light Chain SEQ ID NO: | Clone Name | k$_a$ (1/Ms) | k$_d$ (1/s) | Average KINEXA® values KD |
|---|---|---|---|---|---|
| 4 | 24 | APE265-817/773 | ND | ND | 322 pM |
| 12 | 24 | APE318-878/773 | ND | ND | 14.2 nM |
| 13 | 24 | APE319-887/773 | ND | ND | 6.1 nM |
| 10 | 24 | APE320-847/773 | ND | ND | 2.5 nM |
| 6 | 24 | APE321-844/773 | ND | ND | 9.4 nM |
| 48 | 24 | APE422-1141/773 | 3.60E+05 | 2.40E−05 | 67 pM |
| 37 | 24 | APE467-1138/773 | ND | ND | 374 pM |
| 20 | 24 | APE470-1150/773 | ND | ND | 6.9 nM |
| 64 | 24 | APE480-1261/773 | ND | ND | 1.2 nM |
| 67 | 24 | APE490-1263/773 | ND | ND | 948 pM |
| 53 | 24 | APE498-1330/773 | ND | ND | 126 pM |
| 56 | 24 | APE499-1332/773 | ND | ND | 92 pM |
| 55 | 24 | APE508-1266/773 | 4.18E+05 | 1.80E−05 | 43 pM |
| 42 | 24 | APE545-1346/773 | ND | ND | 270 pM |
| 55 | 81 | APE744-1266/1540 | ND | ND | 875 pM |
| 83 | 24 | APE860-1723/773 | ND | ND | 49 pM |
| 78 | 24 | APE755-1574/773 | 1.20E+06 | 5.90E−06 | 4.9 pM |
| 79 | 24 | APE857-1622/773 | ND | ND | 4.8 pM |

The results of this example demonstrate that an IL-17-binding agent comprising the immunoglobulin heavy and light chain polypeptides described herein can bind to human IL-17 in vitro.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated interleukin-17 (IL-17)-binding agent comprising both of the following:
   (a) an immunoglobulin heavy chain polypeptide comprising SEQ ID NO: 32, SEQ ID NO: 33, SEQ ID NO: 78, or SEQ ID NO: 79 and
   (b) an immunoglobulin light chain polypeptide comprising SEQ ID NO: 24.

2. The isolated IL-17-binding agent of claim 1, which is an antibody, an antibody conjugate, or an antigen-binding fragment thereof.

3. The isolated IL-17-binding agent of claim 2, which is an antibody fragment selected from the group consisting of F(ab')2, Fab', Fab, Fv, scFv, dsFv, dAb, and a single chain binding polypeptide.

4. The isolated IL-17-binding agent of claim 2, which is a human antibody, a non-human antibody, or a chimeric antibody.

5. The isolated IL-17 binding agent of claim 1, which comprises an immunoglobulin heavy chain polypeptide comprising SEQ ID NO: 32.

6. The isolated IL-17 binding agent of claim 1, which comprises an immunoglobulin heavy chain polypeptide comprising SEQ ID NO: 33.

7. The isolated IL-17 binding agent of claim 1, which comprises an immunoglobulin heavy chain polypeptide comprising SEQ ID NO: 78.

8. The isolated IL-17 binding agent of claim 1, which comprises an immunoglobulin heavy chain polypeptide comprising SEQ ID NO: 79.

9. A composition comprising the isolated IL-17-binding agent of claim 1 and a pharmaceutically acceptable carrier.

10. The composition of claim 9, wherein the IL-17-binding agent comprises an immunoglobulin heavy chain polypeptide comprising SEQ ID NO: 32.

11. The composition of claim 9, wherein the IL-17-binding agent comprises an immunoglobulin heavy chain polypeptide comprising SEQ ID NO: 33.

12. The composition of claim 9, wherein the IL-17-binding agent comprises an immunoglobulin heavy chain polypeptide comprising SEQ ID NO: 78.

13. The composition of claim 9, wherein the IL-17-binding agent comprises an immunoglobulin heavy chain polypeptide comprising SEQ ID NO: 79.

14. A vector comprising a nucleic acid sequence encoding the isolated IL-17-binding agent of claim 1.

15. The vector of claim 14, wherein the IL-17-binding agent comprises an immunoglobulin heavy chain polypeptide comprising SEQ ID NO: 32.

16. The vector of claim 14, wherein the IL-17-binding agent comprises an immunoglobulin heavy chain polypeptide comprising SEQ ID NO: 33.

17. The vector of claim 14, wherein the IL-17-binding agent comprises an immunoglobulin heavy chain polypeptide comprising SEQ ID NO: 78.

18. The vector of claim 14, wherein the IL-17-binding agent comprises an immunoglobulin heavy chain polypeptide comprising SEQ ID NO: 79.

19. An isolated cell comprising the vector of claim 14.

20. An isolated cell comprising the vector of claim 15.

21. An isolated cell comprising the vector of claim 16.

22. An isolated cell comprising the vector of claim 17.

23. An isolated cell comprising the vector of claim 18.

* * * * *